United States Patent
Myung et al.

(10) Patent No.: US 10,188,294 B2
(45) Date of Patent: Jan. 29, 2019

(54) ADAPTER FOR RETINAL IMAGING USING A HAND HELD COMPUTER

(71) Applicant: Verana Health, Inc., San Francisco, CA (US)

(72) Inventors: David Myung, Santa Clara, CA (US); David Nicholas Polkinhorne, Portola Valley, CA (US); Benjamin Scott Arnett, Morgan Hill, CA (US); Gary B. Hulme, San Jose, CA (US); Iraklis Kourtis, Larisa (GR)

(73) Assignee: Verana Health, Inc., San Francisco, CA (US)

( * ) Notice: Subject to any disclaimer, the term of this patent is extended or adjusted under 35 U.S.C. 154(b) by 325 days.

(21) Appl. No.: 15/186,266

(22) Filed: Jun. 17, 2016

(65) Prior Publication Data
US 2016/0367135 A1 Dec. 22, 2016

Related U.S. Application Data

(60) Provisional application No. 62/181,547, filed on Jun. 18, 2015.

(51) Int. Cl.
| | |
|---|---|
| A61B 3/14 | (2006.01) |
| H04M 1/02 | (2006.01) |
| A61B 3/10 | (2006.01) |
| A61B 3/12 | (2006.01) |

(52) U.S. Cl.
CPC ............... *A61B 3/145* (2013.01); *A61B 3/10* (2013.01); *A61B 3/1208* (2013.01); *H04M 1/026* (2013.01)

(58) Field of Classification Search
None
See application file for complete search history.

(56) References Cited

U.S. PATENT DOCUMENTS

| | | |
|---|---|---|
| 4,461,551 A | 7/1984 | Blaha |
| 4,586,892 A | 5/1986 | Ichizawa et al. |
| 4,856,892 A | 8/1989 | Ben Tovim |
| 6,766,041 B2 | 7/2004 | Golden et al. |
| 6,889,006 B2 | 5/2005 | Kobayashi |
| 7,806,528 B2 | 10/2010 | Bedell et al. |
| 7,883,210 B2 | 2/2011 | Filar |
| 8,253,787 B2 | 8/2012 | Yamamoto |

(Continued)

FOREIGN PATENT DOCUMENTS

| | | |
|---|---|---|
| CN | 103110401 A | 5/2013 |
| JP | 2004279733 A | 10/2004 |

(Continued)

OTHER PUBLICATIONS

Bastawrous; Smartphone fundoscopy; Ophthalmology; 119(2); pp. 432-433.e2; Feb. 2012.

(Continued)

*Primary Examiner* — William B Perkey
(74) *Attorney, Agent, or Firm* — Shay Glenn LLP

(57) ABSTRACT

An adapter configured to engage with a hand held computer device to allow a camera on the hand held computer device to take a high quality image of an eye. The adapter allows for high quality imaging of the anterior portion of the eye and the posterior portion of the eye. The adapter can include additional modular components such as an optical pathway enclosure and a beamsplitter module.

55 Claims, 46 Drawing Sheets

(56) References Cited

U.S. PATENT DOCUMENTS

| | | |
|---|---|---|
| 8,454,166 B2 | 6/2013 | Fateh |
| 8,511,820 B2 | 8/2013 | Trachtman |
| 8,725,210 B2 | 5/2014 | Yang |
| 8,760,569 B2 | 6/2014 | Yang |
| 8,798,453 B2 | 8/2014 | Lawton |
| 8,836,778 B2 | 9/2014 | Ignatovich et al. |
| 8,862,183 B2 | 10/2014 | Kulas |
| D717,856 S | 11/2014 | Slawson et al. |
| 8,888,288 B2 | 11/2014 | Iravani et al. |
| 8,905,543 B2 | 12/2014 | Davis |
| 8,922,366 B1 | 12/2014 | Honoré et al. |
| 9,019,420 B2 | 4/2015 | Hurst et al. |
| 9,031,610 B2 | 5/2015 | Kulas |
| 9,066,683 B2 | 6/2015 | Zhou |
| 9,149,179 B2 | 10/2015 | Barnard et al. |
| 9,215,977 B2 | 12/2015 | Bitran |
| 2004/0208343 A1 | 10/2004 | Golden et al. |
| 2005/0200707 A1 | 9/2005 | Yogesan et al. |
| 2005/0270484 A1 | 12/2005 | Maeda et al. |
| 2007/0280677 A1 | 12/2007 | Drake et al. |
| 2009/0062686 A1 | 3/2009 | Hyde et al. |
| 2010/0328420 A1 | 12/2010 | Roman |
| 2011/0085138 A1 | 4/2011 | Filar |
| 2011/0299036 A1 | 12/2011 | Goldenholz |
| 2012/0176689 A1 | 7/2012 | Brown |
| 2012/0229617 A1 | 9/2012 | Yates et al. |
| 2012/0320340 A1 | 12/2012 | Coleman |
| 2013/0083185 A1 | 4/2013 | Coleman |
| 2013/0150123 A1 | 6/2013 | Kulas |
| 2013/0293840 A1 | 11/2013 | Bartels |
| 2013/0300919 A1 | 11/2013 | Fletcher et al. |
| 2014/0002792 A1 | 1/2014 | Filar |
| 2014/0071547 A1 | 3/2014 | O'Neill et al. |
| 2014/0078594 A1 | 3/2014 | Springer |
| 2014/0085603 A1 | 3/2014 | Su et al. |
| 2014/0114208 A1 | 4/2014 | Smith et al. |
| 2014/0132932 A1 | 5/2014 | Jung |
| 2014/0228668 A1 | 8/2014 | Wakizaka et al. |
| 2014/0268053 A1 | 9/2014 | Fabian et al. |
| 2014/0327753 A1 | 11/2014 | Prabhakar |
| 2014/0327754 A1 | 11/2014 | Prabhakar |
| 2014/0327755 A1 | 11/2014 | Prabhakar |
| 2014/0350379 A1 | 11/2014 | Verdooner |
| 2015/0002950 A1 | 1/2015 | O'Neill et al. |
| 2015/0042873 A1 | 2/2015 | Hunt |
| 2015/0045012 A1 | 2/2015 | Siminou |
| 2015/0098060 A1 | 4/2015 | Zhou |
| 2015/0103317 A1 | 4/2015 | Goldfain et al. |
| 2015/0104087 A1 | 4/2015 | Katuwal et al. |
| 2015/0223678 A1 | 8/2015 | Goldfain et al. |
| 2015/0223686 A1 | 8/2015 | Wang |
| 2015/0254524 A1 | 9/2015 | Dickrell et al. |
| 2015/0257639 A1 | 9/2015 | Manquez Hatta et al. |
| 2015/0313462 A1 | 11/2015 | Reis |
| 2016/0113489 A1 | 4/2016 | Nugent et al. |
| 2016/0367135 A1 * | 12/2016 | Myung ................. A61B 3/145 |
| 2017/0280996 A1 | 10/2017 | Myung et al. |
| 2018/0116509 A1 * | 5/2018 | Myung ................... A61B 3/10 |

FOREIGN PATENT DOCUMENTS

| | | |
|---|---|---|
| JP | 2006212102 A | 8/2006 |
| JP | 2008093118 A | 4/2008 |
| JP | 2008295725 A | 12/2008 |
| JP | 2013104986 A | 5/2013 |
| JP | 2005524462 A | 8/2018 |
| WO | WO 03/043363 A1 | 5/2003 |
| WO | WO2007/069294 A1 | 6/2007 |
| WO | WO2012/176960 A1 | 12/2012 |
| WO | WO2014/181096 A1 | 11/2014 |
| WO | WO2015/035229 A2 | 3/2015 |
| WO | WO2015/054672 A1 | 4/2015 |
| WO | WO2015071779 A1 | 5/2015 |

OTHER PUBLICATIONS

Chakrabarti; Application of mobile technology in ophthalmology to meet the demands of low-resource settings; Journal of Mobile Technology in Medicine; 1(4S); pp. 1-3; Dec. 2012.

Chhablani et al.; Smartphones in ophthalmology; Indian J. Ophthalmol.; 60(2); pp. 127-131; Mar./Apr. 2012 (Author Manuscript).

Echanique et al.; Ocular Cellscope; University of California at Berkeley; Electrical engineering and computer sciences; 23 pages; retrieved from the internet (http://digitalassets.lib.berkeley.edu/techreports/ucb/text/EECS-2014-91.pdf); May 16, 2014.

Haddock et al.; Simple, inexpensive technique for high-quality smartphone fundus photography in human and animal eyes; Journal of Ophthalmology; 2013; pp. 1-5; published online Sep. 19, 2013.

Hester et al.; Smart Phoneography—how to take slit lamp photographs with an iphone; 12 pages; retrieved Jul. 30, 2015 from the internet (http://eyewiki.aao.org/Smart_Phoneography_-_How_to_take_slit_lamp_photographs_with_an_iPhone).

Kim et al.; Smartphone photography safety; Ophthalmology; 119(10); pp. 220-2201; Oct. 2012.

Lord et al.; Novel uses of smartphones in ophthalmology; Ophthalmology; 117(6); pp. 1274-1274 e3; Jun. 2010.

Teichman et al.; From iphone to eyephone: a technique for photodocumentation; Can. J. Ophthalmol.; 46(3); pp. 284-286; Jun. 2011.

Myung et al.; U.S. Appl. No. 15/560,873 entitled "Modular adapters for mobile ophthalmoscopy," filed Sep. 22, 2017.

* cited by examiner

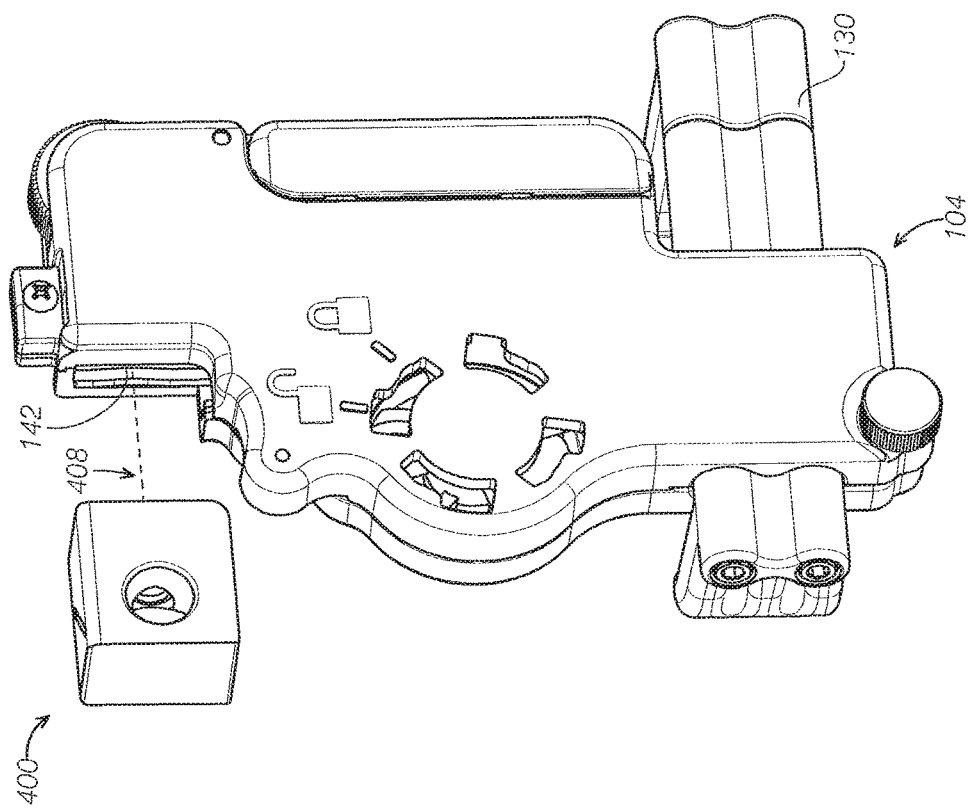
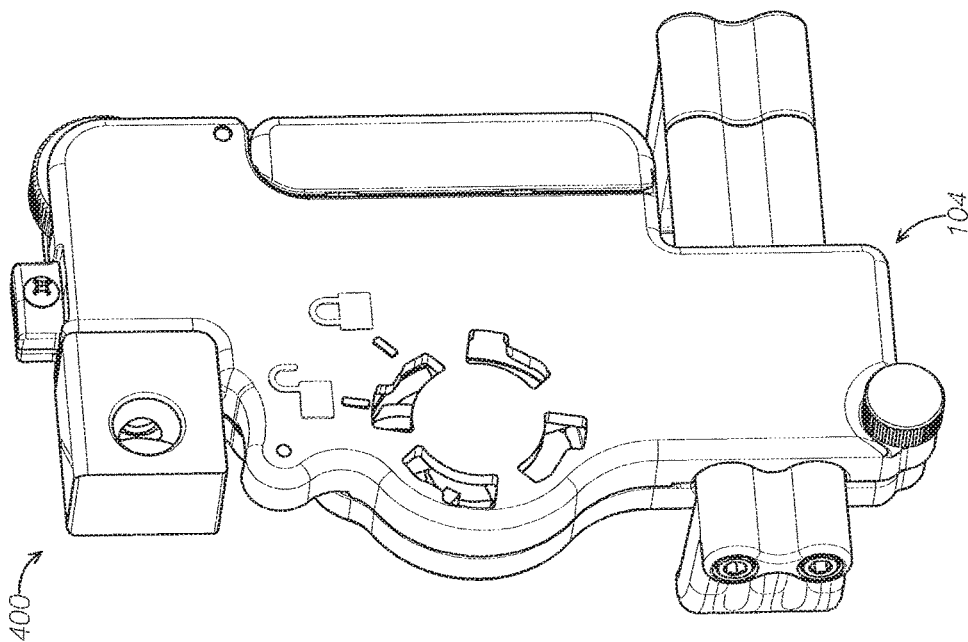

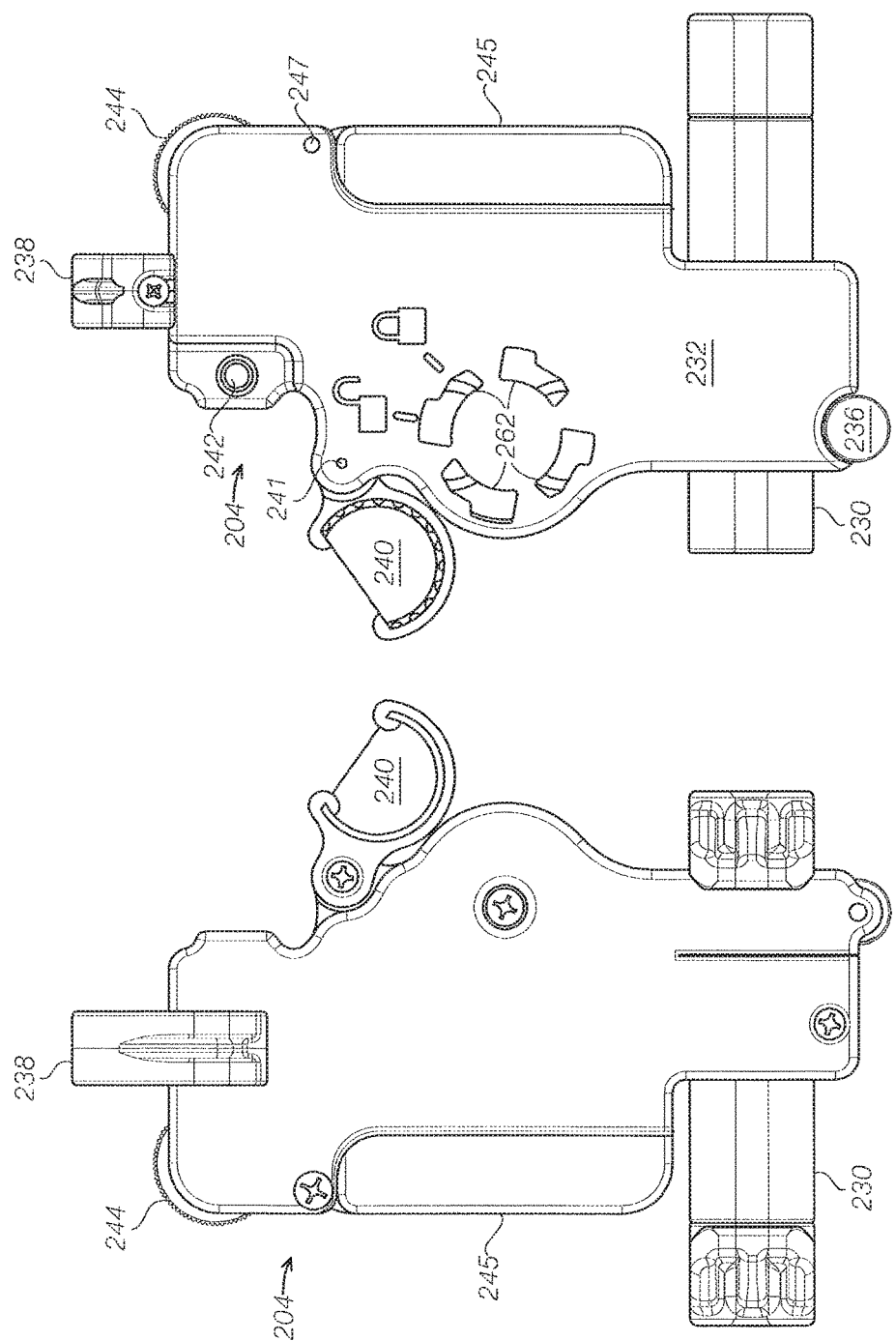

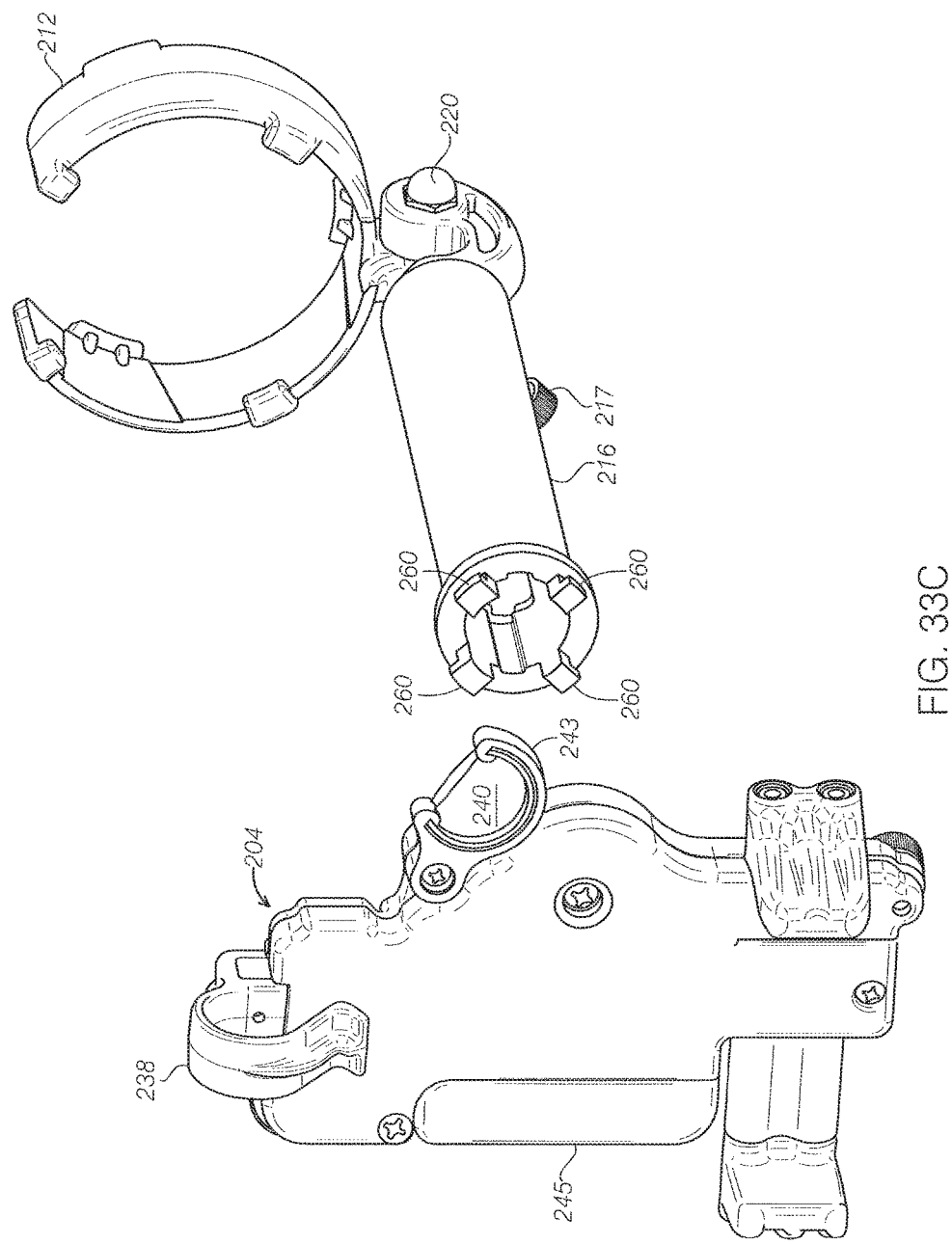

ADAPTER FOR RETINAL IMAGING USING A HAND HELD COMPUTER

CROSS REFERENCE TO RELATED APPLICATIONS

This application claims the benefit of U.S. Provisional Patent Application No. 62/181,547, filed Jun. 18, 2015, titled "ADAPTER FOR RETINAL IMAGING USING A HAND HELD COMPUTER" which is herein incorporated by reference in its entirety.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD

The present application relates generally to the field of ophthalmoscopes and retinal imaging.

BACKGROUND

Various smartphone adapters for retinal imaging are known, including those disclosed in US 2012/0320340 and WO 2014/194182. However, a need exists for improved adapters for use with hand held computer devices that have improved reliability and usability in a light weight, rugged, and low cost package.

SUMMARY OF THE DISCLOSURE

The present invention relates to an adapter that is configured to engage with a hand held computer device for retinal imaging.

In general, in one embodiment an adapter configured to engage with a hand held computer device with a camera having an optical axis including an anterior adapter portion including a body, a clamp configured to engage with the hand held computer device at a first location and a second location, a lens holder engaged with a macro lens movable between a first position in the optical axis of the camera and a second position outside of the optical axis of the camera, an adjustable light source with a light axis parallel to a macro lens optical axis, a third engagement surface configured to slidably engage with the hand held computer device at a third location, and a complementary surface of the body configured to reversibly engage with a base section of a posterior portion, wherein the clamp defines an axis and the body of the anterior adapter portion is configured to move along the axis of the clamp; and the posterior portion including the base section configured to reversibly engage with the complementary surface of the body of the anterior adapter portion, a telescoping section movable relative to the base section, and a lens holder engaged with a distal end of the telescoping section configured to removably engage with an ophthalmoscopy lens, the base section configured to removably engage with the body of the anterior adapter portion to form an optical axis between the ophthalmoscopy lens and the camera of the hand held computer device.

This and other embodiments can include one or more of the following features. The adapter can further include a lens holder hinge engaged with the telescoping section of the posterior portion and the lens holder. The lens holder hinge can be adapted to move the lens holder between a first position in the optical axis of the camera and a second position outside of the optical axis of the camera. The second position can include the lens holder folded flush with the telescoping section. The adapter can have an open optical pathway between the lens holder and camera. The third engagement surface can have a semi-circular or hook shape configured to slidably engage with the hand held computer device at the third location. The third engagement surface can be adapted to hold a surface of the body of the anterior adapter against a surface of the hand held computer device. The adapter can further include a removable enclosure configured to removably engage with the posterior portion. The removable enclosure can include a clamping mechanism to engage with the posterior portion. The removable enclosure can further include a telescoping portion configured to adjust a length of the removable cover. The removable enclosure can further include a proximal portion with an opening to accommodate the camera of the hand held computer device and the light source of the anterior adapter portion and a distal section to engage with the lens holder. The removable enclosure can be adapted to encase the optical pathway between the camera and the lens holder. The adapter can further include an ophthalmoscopy lens engaged with the lens holder, the ophthalmoscopy lens configured for indirect ophthalmoscopy. The ophthalmoscopy lens can be a lens in the range of 10 D to 90 D. The macro lens can have a dominant plane orthogonal to the optical axis of the macro lens. The macro lens can have a non-circular cross-sectional profile in the dominant plane. The adjustable light source can be integral with the body of the anterior adapter and powered by a power source within the anterior adapter. The light source can include a light-emitting diode (LED). The adapter can further include a light diffuser. The adapter can further include a light source control on the anterior adapter portion configured to adjust the properties of the light source. The light source control can include a dial. The clamp can include a first surface configured to engage with the first location of the hand held computer device and a second surface configured to engage with the second location of the hand held computer device. The first surface and second surface can be on opposing sides of the hand held computer device. The adapter can further include an anterior locking mechanism on the anterior adapter portion configured to position the anterior body relative to the axis of the clamp. The anterior locking mechanism can be adapted to secure a length of the axis of the clamp. The anterior locking mechanism can be configured to secure the first surface of the clamp relative to the second surface of the clamp. The adapter can further include a posterior locking mechanism configured to secure the telescoping section relative to the base section. The adapter can further include a lens holder locking mechanism configured to secure the lens holder relative to an axis of the telescoping section. The locking mechanism can include a thumb screw. The adapter can further include a battery compartment within the body of the anterior adapter portion. The clamp can be spring loaded. The clamp can be configured to apply a compressive force to the first and second location. The adapter can further include a beam splitter module configured to removably engage with the anterior adapter. The beam splitter module when engaged with the anterior adapter can be configured to direct light from the adjustable light source to be coaxial with the optical axis of the camera. The beam splitter can include a mirror to reflect light from the adjustable light source to be coaxial with the optical axis of the camera. The beam splitter module can further include a polarizing light filter in the optical pathway of the adjustable light source when the beam splitter module is engaged with the anterior adapter portion and a polarizing light filter in the optical pathway of the camera when the beam splitter module is engaged with the anterior adapter portion. The adapter can further include a slit beam module configured to removably engage with the anterior adapter that refracts and filters the light emitted by the light source into a rectangular slit shape. The adapter can further include a cobalt blue filter adapted to be positioned over the LED and/or the camera lens when the anterior adapter portion is engaged with the hand held computer device. The hand held computer device can be a smartphone, tablet computer, or mobile imaging device. The third engagement structure can be configured to removably engage with the anterior adapter portion. The third engagement structure can further include an adjustable engagement mechanism configured to engage with the hand held computer device. The adjustable engagement mechanism can further include a thumb screw and a hand held computer engagement surface. The adjustable engagement mechanism can further include a spring, a hand held computer engagement surface, and a release lever. The adapter can further include a light shaping module configured to be removably engaged with the anterior adapter portion to modify the adjustable light source. The light shaping module can include a plurality of light shaping structures. The light shaping module can include a first aperture, a second aperture that is larger than the first aperture, a slit lamp, and a blue filter. The telescoping section can have a closed optical pathway. The base section can include a magnet to engage with the anterior adapter portion.

In general, in one embodiment, a method of obtaining images of an eye of a patient, the method including attaching an anterior adapter portion to a hand held computer device having a camera, the anterior adapter including a body, a clamp configured to engage with the hand held computer device at a first location and a second location, a lens holder engaged with a macro lens movable between a first position in the optical axis of the camera and a second position outside of the optical axis of the camera, an adjustable light source with a light axis parallel to a macro lens optical axis, a third engagement surface configured to slidably engage with the hand held computer device at a third location, and a complementary surface of the body configured to reversibly engage with a base section of a posterior portion, wherein the clamp defines an axis and the body of the anterior adapter portion is configured to move along the axis of the clamp; adjusting a position of the body of the anterior adapter relative to the axis of the clamp to line up the macro lens optical axis with the optical axis of the camera of the hand held computer device; obtaining an image of the eye of the patient with the camera of the hand held computer device using the macro lens and the adjustable light source; engaging a posterior portion to the anterior adapter portion by engaging the base section of the posterior portion with the complementary surface of the body of the anterior adapter portion, the posterior portion including a telescoping section movable relative to the base section, and a lens holder engaged with a distal end of the telescoping section configured to removably engage with an ophthalmoscopy lens, the base section configured to removably engage with the body of the anterior adapter portion to form an optical axis between the ophthalmoscopy lens and the camera of the hand held computer device; and obtaining an image of the eye of the patient with the camera of the hand held computer device and the ophthalmoscopy lens.

This and other embodiments can include one or more of the following features. The method can further include locking the position of the body of the anterior adapter after adjusting the position of the body of the anterior adapter relative to the axis of the clamp to line up the macro lens optical axis with the optical axis of the camera of the hand held computer device. The method can further include engaging an ophthalmoscopy lens with the lens holder prior to obtaining the image of the eye of the patient with the camera of the hand held computer device and the ophthalmoscopy lens. The method can further include engaging a removable cover with the posterior portion to encase an optical pathway between the ophthalmoscopy lens and the camera of the hand held computer device. The method can further include adjusting the adjustable light source of the anterior adapter portion to illuminate the eye of the patient with a desired amount of light. The method can further include engaging a beam splitter module with the anterior adapter. The beam splitter module can be configured to removably engage with the anterior adapter. The beam splitter module when engaged with the anterior adapter can be configured to direct light from the adjustable light source to be coaxial with the optical axis of the camera. The method can further include obtaining a direct ophthalmoscopy image of the eye of the patient with the camera of the hand held computer device and the beam splitter module. The method can further include engaging a slit beam module with the anterior adapter. The slit beam module can be configured to removably engage with the anterior adapter portion. The method can further include obtaining an image of the eye of the patient with the slit beam module. The hand held computer device can be a smartphone, tablet computer, or mobile imaging device.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIGS. 26C and 26D illustrate the beam splitter module separate from and engaged with an anterior adapter, respectively, in accordance with some embodiments.

FIGS. 30A-30D illustrate various views of an anterior adapter portion in accordance with some embodiments including a front-view, cross-sectional view, back view and front view, respectively.

FIGS. 33A-33C illustrate various views of an anterior adapter portion engaged with a hand held computer device with the posterior portion separate from the anterior portion in accordance with some embodiments.

DETAILED DESCRIPTION

Figure 1:
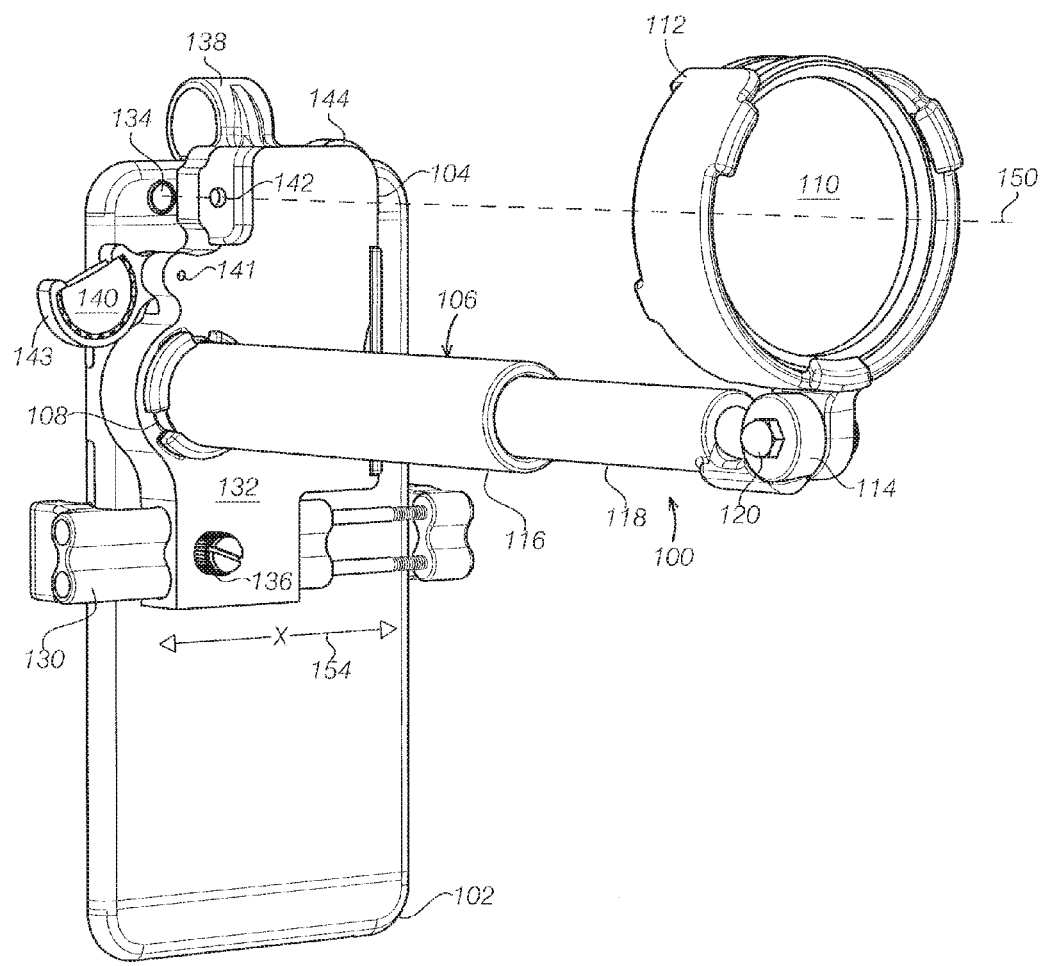
FIG. 1 is a front view of an adapter attached to a hand held computer device in accordance with some embodiments.

Adapters are disclosed herein for use with hand held computer devices to allow a physician, medical professional, nurse, technician, or any user to take an image of a retina of a patient or user. The adapter can engage with the hand held computer device such that a camera on the hand held computer device can line up with an optical axis of the adapter to take a high quality image of the retina. The adjustability of the adapter can allow for the use of the adapter with a variety of different hand held computer devices having cameras located at different areas of the hand held computer devices. Examples of hand held computer devices that can be used with the adapters disclosed herein include tablet computers (iPad®, galaxy note, iPod®, etc.), smartphone devices (Apple® iPhone®, Motorola devices, Samsung devices, HTC devices, etc.), mobile imaging devices, or other electronic devices with a camera.

The light sources on hand held computer devices are typically too bright to illuminate the patient's eye without causing discomfort to the patient. The adapters disclosed herein can include an adjustable light source as part of the anterior adapter. The adjustable light source can easily be adjusted to provide the desired level of light to illuminate the eye of the patient. Another advantage of the inclusion of an adjustable light source on board the adapter is the improvement of the regulatory approval of the device in the U.S. An adapter that uses the light source of the camera of the hand held computer device can require separate regulatory approval for each different model of hand held computer device to show that the light source is safe for use with the eye. The inclusion of the adjustable light source eliminates variability between the light sources for different hand held computer devices and streamlines the regulatory approval process in the U.S.

WO 2014/194182 discloses a modular lens adapter system for anterior and posterior segment ophthalmoscopy with separate adapters for the anterior imaging and posterior imaging. Lining up the optical axis of the posterior ophthalmoscopy lens, the light source, and the camera can provide some challenges in the field and make the device more difficult to use. The present disclosure discovered that combining the anterior segment adapter and the posterior segment adapter greatly simplified the use of the device by eliminating additional steps to line up the optical axes of the different pieces of the system. The fixed relationship between the optical axis of the anterior adapter portion and the optical axis of the ophthalmoscopy lens greatly simplifies the ease of use of the adapter system and can improve image quality.

The adapter systems described herein can be used to obtain images of the eye of the patient that are comparable to the images obtained using expensive equipment typically only found in doctor's offices. The images obtained using the adapter systems described herein can be used for treatment, diagnosis, and triage purposes.

The portability, ease of use, rugged construction, and low cost enable the adapter systems described herein to be used with a hand held computer to obtain images of the patient's eyes at the doctor's office and outside of the doctor's office. For example, the systems can be used inside and outside in locations lacking a doctor's office or other healthcare provider. The suitability of the adapters for outdoor use allows for a healthcare provider to travel to remote locations to treat patients that lack access to healthcare facilities. The adapter systems can also be used by a general practitioner to send to an ophthalmologist for diagnosis and referral based on the absence or presence of a medical problem with the eye visible in the captured images.

The adapter systems can be configured to removably engage with a hand held computer device with a camera having an optical axis. The adapter systems can include an anterior adapter portion and a posterior portion. The anterior adapter portion can include a body, a clamp configured to removably engage with the hand held computer device, a lens holder, an adjustable light source, a third engagement surface configured to slidably engage with the hand held computer device, and a complementary surface on the body configured to reversibly engage with a portion of the posterior portion.

The clamp can be configured to contact the hand held computer device at a first and second location. In some embodiments the first and second location are on opposing surfaces of the hand held computer device. The clamp can define an axis and allow for the body of the anterior adapter portion to move along the axis of the clamp to line up the optical axis of the camera with the optical axis of the lens in the lens holder.

The lens holder can be adapted to support a macro lens. The lens holder can include a hinge such that the lens holder can move between a first position in the optical axis of the camera and a second position outside of the optical axis of the camera. In some embodiments the macro lens can have a circular dominant cross-section. In other embodiments the macro lens has a dominant plane orthogonal to the optical axis of the macro lens with a non-circular cross-sectional profile. The macro lens can have the non-circular cross section with a portion of the lens removed to adjust the engagement between the macro lens/lens holder and a surface of the body of the anterior adapter portion.

In some embodiments a plurality of the modules described herein, such as the beam splitter module, slit beam module, blue filter, different sized apertures, etc. can be removably engaged with the anterior adapter portion. In some embodiments one or more of the modules can engage with the anterior adapter with a hinge or through a plurality of hinged parts, like in a Swiss army knife. The modules can swing into place and be used and then moved out of the way of the optical path or light source path. For example, the modules could be used in the order of direct ophthalmoscopy with the beam splitter module, followed by the slit beam module, followed by the blue light filter. The modules can be attached along a hinge with a common axis like in a Swiss army knife type configuration. In other cases the modules can each be attached at a different hinge that is adapted to move the module into and out of the desired position (e.g. in the optical pathway or light pathway). For example some modules could engage with the hinge 141. Other modules could engage with a hinge on the back side of the anterior adapter portion to cover the optical pathway or light source. In other embodiments the modules can be removably attached and interchangeable in place of one another, for example the modules can engage with a common section of the anterior adapter. Examples of engagement types include magnets, reversible engagement through complementary mating surfaces, snap on or friction fits, etc.

The adjustable light source can have a light axis parallel to an optical axis of the macro lens or other lens in the lens holder and/or an optical axis of the camera of the hand held computer. In some embodiments the light axis of the adjustable light source can be perpendicular or orthogonal to the optical axis of the camera.

The third engagement surface can be configured to slidably engage with the hand held computer device at a third location. The third engagement can secure the anterior portion relative to the hand held computer device after the optical axis of the camera and the anterior adapter portion have been lined up.

The posterior portion can include a base section configured to reversibly engage with the complementary surface of the body of the anterior adapter portion, a telescoping section movable relative to the base section, and a lens holder engaged with a distal end of the telescoping section configured to removably engage with an ophthalmoscopy lens. The base section can be configured to removably engage with the body of the anterior adapter portion to form an optical axis between the ophthalmoscopy lens and the camera of the hand held computer device.

The lens holder can be engaged with an ophthalmoscopy lens. When the system is not in use the ophthalmoscopy lens can be removed from the lens holder. The ophthalmoscopy lens can be configured for indirect ophthalmoscopy. The lens mount can be sized to accommodate an ophthalmoscopy lens in the range of 10 D to 90 D, such as a 14 D, 20 D, 22 D, 28 D, 30 D, 40 D, or 54 D, 60, 66, and 90 D condensing lens for indirect ophthalmoscopy. The working distance between the lens mount and the hand held computer device can be about 5.75" in the case of an iPhone and a Volk Panretinal 2.2 lens, but will vary depending on the combination of hand held computer device camera, ophthalmoscopy lens power, and the subject being examined. For instance, for certain combinations of patients and lenses, the working distance can be reduced approximately 2 inches, or lengthened to approximately 10 inches. Ophthalmoscopy lenses can be easily mounted and removed from the inner diameter of the lens holder.

The lens holder can be engaged with a lens holder hinge that is engaged with the telescoping section of the posterior portion. The lens holder hinge can provide for movement of the lens holder between a first position in the optical axis of the camera and a second position outside of the optical axis of the camera. The second position can include a position where the lens holder is folded flush with the telescoping section.

The clamp and third engagement structures of the anterior adapter portion allow for the optical axis of the anterior adapter to be moved along the x-axis 154 and y-axis 156 relative to the hand held computer device. The optical axis of the anterior adapter can be adjusted to line up with the optical axis of the camera of the hand held computer device.

The clamp includes a first surface configured to engage with the first location of the hand held computer device and a second surface configured to engage with the second location of the hand held computer device. The first surface and second surface can include a rubber surface or other surface to increase friction and prevent relative movement between the first and second surfaces and the hand held computer device. The first surface and second surface can be on opposing sides of the hand held computer device. In some embodiments the clamp is spring loaded. In some embodiments the clamp is configured to apply a compressive force to the first and second location.

The third engagement surface for the hand held computer device can include a hook or semi-circular shape. In some embodiments the third engagement surface has a semi-circular or hook shape configured to slidably engage with the hand held computer device at the third location. The third engagement surface can be adapted to hold a surface of the body of the anterior adapter against a surface of the hand held computer device. Different sized third engagement surfaces can be used to accommodate hand held computer devices with different camera locations.

In some embodiments the third engagement structure is configured to removably engage with the anterior adapter portion. The adapter system can include a plurality of different third engagement structures that can be have different geometries. The third engagement structure with the desired geometry can be selected based on the location of the camera on the hand held computer device and the dimensions of the hand held computer device.

In some embodiments the third engagement structure can include an adjustable engagement mechanism configured to engage with the hand held computer device. The adjustable mechanism can assist with securing the third engagement structure relative to the hand held computer device and can help accommodate hand held computer devices of varying thickness. In some embodiments the adjustable engagement mechanism can include a thumb screw and a hand held computer engagement surface with the thumb screw being adjusted to provide a compressive force on the hand held computer device with the engagement surface. In some embodiments the adjustable engagement mechanism can include a spring, a hand held computer engagement surface, and a release lever. The spring can provide a compressive force on the hand held computer device and the release lever can be used to quickly disengage the adjustable engagement mechanism.

Once the anterior adapter portion has been positioned to line up the optical axis with the optical axis of the camera the adjustable positions can be secured with a plurality of locking mechanisms to prevent or limit further relative movement between the hand held computer device and adapter.

The adapters can include an anterior locking mechanism on the anterior adapter portion configured to position the anterior body relative to the axis of the clamp. The anterior locking mechanism can be adapted to secure a length of the axis of the clamp such as by securing the first surface of the clamp relative to the second surface of the clamp. The anterior locking mechanism can also secure the body relative to the first surface and second surface of the clamp. In some embodiments the anterior locking mechanism is a thumb screw mechanism.

The posterior portion can also include a locking mechanism to secure the telescoping section relative to the base section of the posterior portion. In some embodiments a thumb screw locking mechanism can be used to secure the telescoping section. In other embodiments a friction fit can be used between the telescoping section and the base section. In some embodiments the telescoping section can move with a twisting motion similar to the structures used in SLR camera lenses.

The posterior portion can also include a lens holder locking mechanism configured to secure the lens holder relative to an axis of the telescoping section. For example the lens holder can be secured when the lens holder engages with an ophthalmoscopy lens to hold the ophthalmoscopy lens in the optical axis of the camera. The lens holder can also be secured when in a folded configuration flush with the telescoping section. The lens holder locking mechanism can include a thumb screw mechanism.

The flashes used on many hand held computer devices are often too bright for most patient eyes, and/or they are too variable in their characteristics from device to device to be reliably or safely used at the discretion of a user. The adjustable light source on the anterior adapter portion provides a softer amount of light to the eye of the patient so that high quality images can be obtained while minimizing or eliminating patient discomfort from the light source. The use of an the adjustable light source on the anterior adapter portion with a softer amount of light made it easier to comply with regulatory authorities to show the amount of light provided to the eye was safe. Yet another benefit of the adjustable light source on the anterior portion is that it eliminates variability between the light sources on different hand held computer devices. The use of an adjustable light source on the anterior adapter portion also streamlined the regulatory review process for the device because the same adjustable light source of the anterior adapter portion is used with any of the hand held computer devices. As a result the adjustable light source could be reviewed for safety once with the anterior adapter portion subsequently approved for use with any hand held computer device versus regulatory review and approval for each light source on each hand held computer device to be used with the adapter.

The adjustable light source is integral with the body of the anterior adapter and powered by a power source within the anterior adapter. In some embodiments the light source comprises a light-emitting diode (LED). In some embodiments a light diffuser can be used with the adjustable light source. In some embodiments the anterior adapter portion includes a light source control configured to adjust the properties of the light source. In one example the light source control is a dial. In other examples the light source control is a slider or a set of buttons, e.g. a plus and minus button to increase or decrease the intensity. The anterior adapter can include a battery compartment within the body of the anterior adapter portion to power the adjustable light source.

In some cases an open optical pathway between the lens holder and the camera can be used when imaging the retina. This configuration can be used in lower light environments, such as those that can be present indoors or in a doctor's office or healthcare provider office.

Figure 29A:
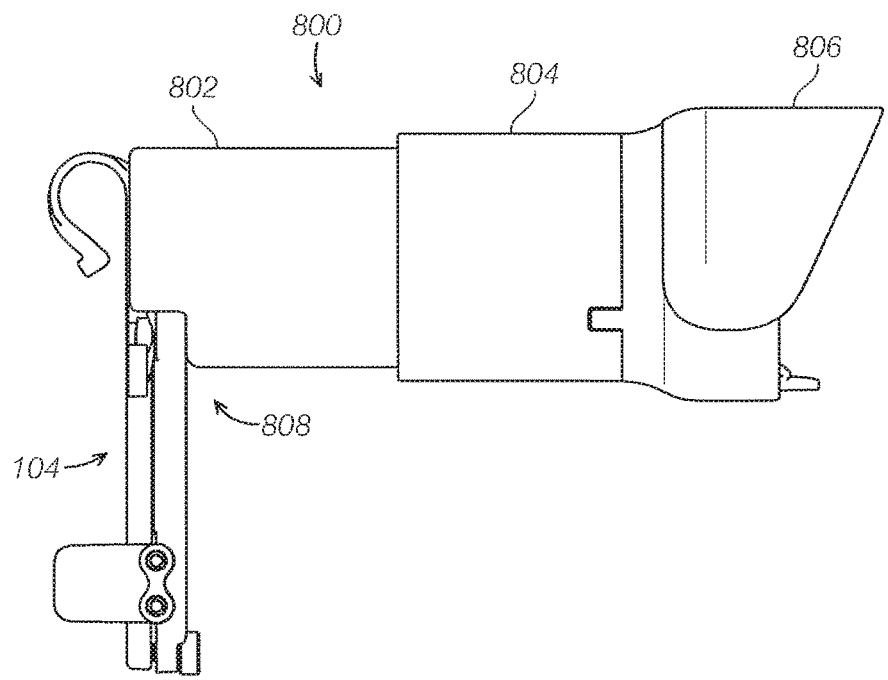
FIG. 29A illustrates an adapter with a posterior portion having an integral telescoping optical pathway enclosure in accordance with some embodiments.
Figure 29B:
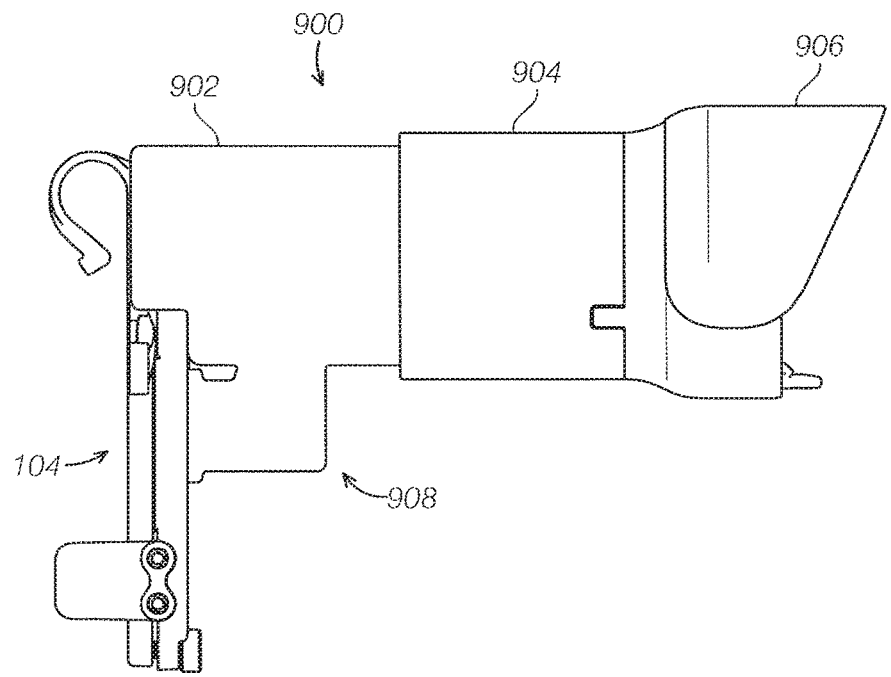
FIG. 29B illustrates an adapter with a posterior portion having an integral telescoping optical pathway enclosure in accordance with some embodiments.
Figure 30B:
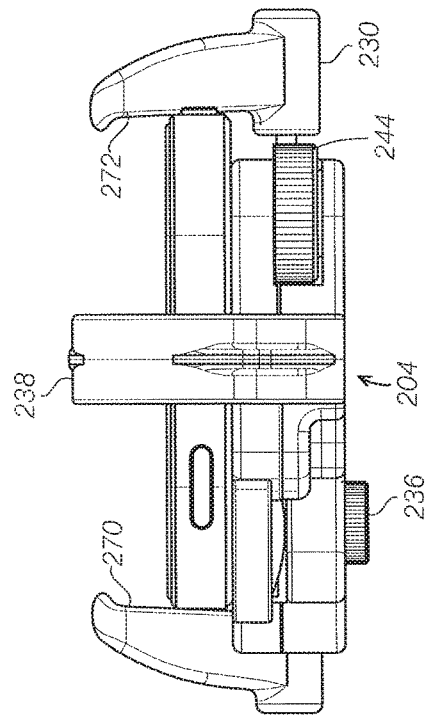
Figure 30A:
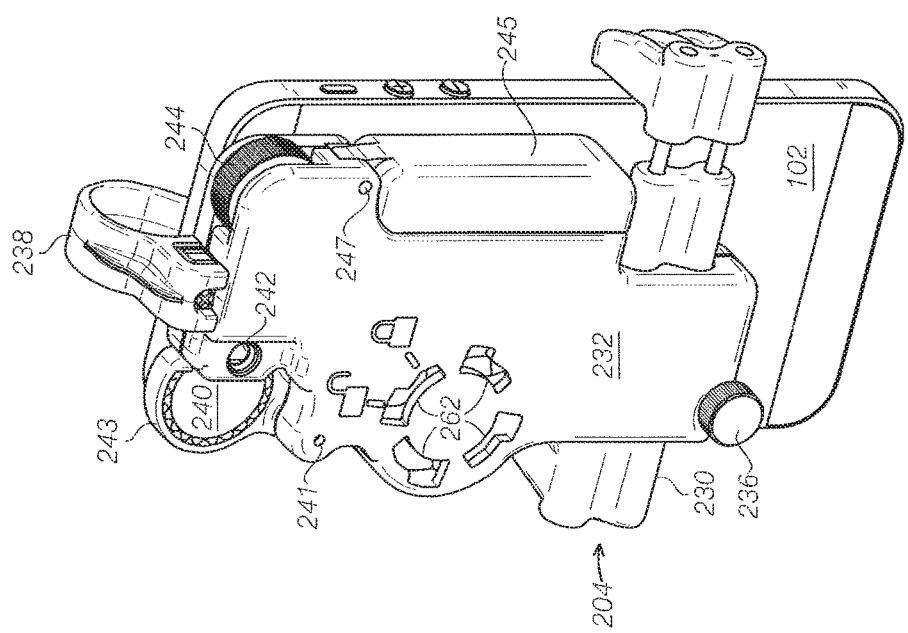

In some cases, such as outdoor settings where examinations can be performed in poorer countries and remote settings away from healthcare facilities, a cover can be used to block exterior light along the optical pathway between the camera and the ophthalmoscopy lens and posterior lens holder. Reducing or blocking the exterior light can improve the image quality and brightness of images of the patient's eyes. In some embodiments a removable cover configured to removably engage with the posterior portion is used to form an enclosure to reduce and block light from the optical pathway. The removable cover can include a clamping mechanism to engage with the posterior portion, such as the telescoping section. The removable cover can also include a telescoping portion configured to adjust a length of the removable cover to match the length of the telescoping section. For example, when the telescoping section is adjusted to improve the image of the retina in the ophthalmoscopy lens the cover length can move with the movement of the telescoping section. The removable cover can include a proximal portion with an opening to accommodate the camera of the hand held computer device and the light source of the anterior adapter portion and a distal section to engage with the lens holder. The distal section of the cover can include a groove or opening to engage with the lens holder hinge to receive all or a portion of the lens holder within an internal volume of the cover. The telescoping can be accomplished through a twisting or sliding mechanism. In some embodiments telescoping can be automated through the use of a wirelessly controlled motor. In some embodiments a second lens can also be positioned within the enclosure to create a compound lens optical pathway. In some embodiments the enclosure portion itself can telescope and a separate telescoping section is not used. For example the telescoping enclosure can direct engage with the anterior adapter portion as shown in FIGS. 29A and 29B.

The adapter systems can be combined with modular units to obtain additional images of the eye. For example, a beam splitter module can be used for direct ophthalmoscopy of the eye. A slit lamp module can be used to obtain optical cross-sectional images of the cornea and anterior chamber of the eye.

In some embodiments a beam splitter module is provided for use with the adapters disclosed herein. The beam splitter module can be configured to removably engage with the anterior adapter. The beam splitter module, when engaged with the anterior adapter, is configured to direct light from the adjustable light source to be coaxial with the optical axis of the camera. The beam splitter can include one or more mirrors to reflect light from the adjustable light source to be coaxial with the optical axis of the camera. The beam splitter can also include a polarizing light filter in the optical pathway of the adjustable light source when the beam splitter module is engaged with the anterior adapter portion. The beam splitter can also include a polarizing light filter in the optical pathway of the camera when the beam splitter module is engaged with the anterior adapter portion. A polarizing light filter can also be placed over the LED light source as well as in combination with the polarizing light filter over the camera lens, or used alone over the LED.

In some embodiments a slit beam module configured to removably engage with the anterior adapter can be used with the adapter. The slit beam module can be engaged with the anterior adapters described herein to provide for some of the functionality of a conventional slit lamp device. The slit beam module creates a rectangular beam of light using a spherocylindrical lens, a rectangular aperture, or both. The slit beam module either approaches the eye at a fixed angle relative to the optical pathway, or with an adjustable angle. The aspect ratio of the rectangular beam is also optionally adjustable to a size of 0.5 mm×0.5 mm, to a longer aspect ratio such as 15 mm×0.5 mm to 14 mm×5 mm, or as large as 15 mm×15 mm out to diffuse lighting such that there can be little or no perceivable borders.

In some embodiments the systems can include a light shaping module configured to be removably engaged with the anterior adapter portion to modify the adjustable light source. The light shaping module includes a plurality of light shaping structures. In one example the light shaping module can include one or more of: a first aperture, a second aperture that is larger than the first aperture, a convex lens, a plano-convex lens, a spherocylindrical lens, a slit lamp, and a blue filter.

In some embodiments the base section includes a magnet to engage with the anterior adapter portion. The anterior adapter portion can include a complementary magnet to engage with and line up the posterior portion such that the posterior portion has the desired orientation relative to the optical pathway of the anterior adapter portion. In some embodiments the magnets can be used in addition to separate complementary engagement surfaces, such as a groove and male counterpart to the groove.

In some embodiments the telescoping section has a closed optical pathway. The closed optical pathway can include a built in ophthalmoscopy lens.

Methods are also provided for using the adapters described herein to capture images of the anterior segment and posterior segment of the eye of a patient. For example the anterior adapter portion can be engaged with and lined up with the optical axis of the camera of the hand held computer device. The macro lens and lens holder can be moved to a position in the optical axis of the camera. Next, the hand held computer device and adapter can be positioned to capture an image of the anterior segment of the eye of the patient using the camera, adjustable light source, and the macro lens. After the macro lens has been used the macro lens holder can be moved to a position outside of the optical axis of the camera. For imaging the retina, the posterior portion can be engaged with and secured relative to the anterior adapter portion. An ophthalmoscopy lens is engaged with the lens holder. Next, the length of the telescoping section can be adjusted to properly focus the ophthalmoscopy lens on the desired portion of the eye of the patient. The adjustable light source can also be adjusted to provide the desired illumination to the eye of the patient. An image of the retina of the patient can then be captured with the camera and the ophthalmoscopy lens. The posterior adapter is typically used on a patient with a dilated pupil (e.g. through the use of a topical mydriatic agent).

For bright outdoor or bright indoor settings the removable cover can be used. The removable cover can be engaged with the posterior portion followed by adjusting the length of the telescoping section and adjustable light source to obtain an image of the patient's eye through the ophthalmoscopy lens.

For direct ophthalmoscopy the beam splitter module adapter can be engaged with the anterior adapter portion.

The beam splitter can be engaged with the adjustable light source to reflect the light emitted from the adjustable light source to be coincidental with the optical axis of the camera of the hand held computer device. The optical axis of the camera can be used to direct the path of the light source through the pupil of the eye of the patient without dilation (e.g. non-mydriatic) to obtain an image of the retina of the patient via direct ophthalmoscopy.

Examples of a hand held slit lamps along with methods for using such a hand held slit lamps are disclosed in U.S. Pat. No. 4,461,551, the disclosure of which is incorporated by reference in its entirety herein.

FIG. 1 is a front view of an adapter 100 attached to a hand held computer device 102 in accordance with some embodiments. The adapter 100 includes an anterior adapter portion 104 and a posterior portion 106. The posterior portion 106 can be configured to removably engage with the anterior adapter portion 104 at a base 108. The posterior portion 106 includes a lens 110 (such as an ophthalmoscopy lens) and lens holder 112. The posterior portion 106 can include a base shaft 116 and telescoping shaft 118 configured to move relative to one another to modify the length of the posterior portion 106. The lens holder 112 can be connected to the telescoping shaft 118 at an adjustable hinge 114. The hinge 114 can be secured with an adjustable locking screw 120. The adjustable screw 120 can also be configured to lock the movement of the telescoping shaft 118 relative to the base shaft 116 in some embodiments.

Figure 5:
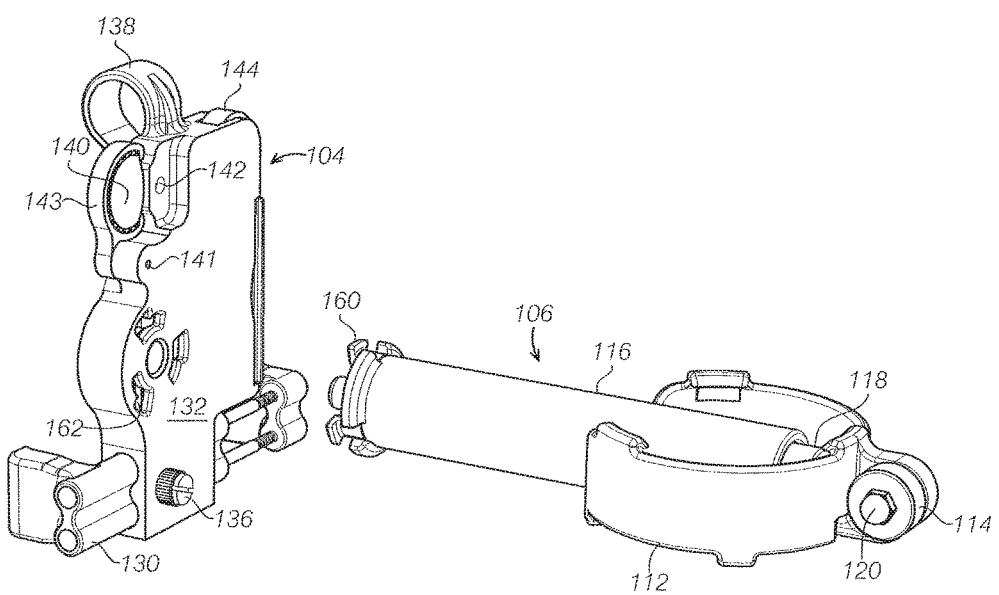
FIG. 5 illustrates an anterior portion and posterior portion of an adapter in accordance with some embodiments.

The anterior adapter portion 104 can be configured to receive the base shaft 116 at base 108, such as with the complementary mating surface 162 shown in FIG. 5. The anterior adapter portion 104 can be configured to engage with the hand held computer device at multiple contact points. For example, the illustrated adapter 100 engages the hand held computer device at three contact points. The adapter 100 can be configured to be movable relative to the hand held computer device along a vertical y-axis 156 and horizontal x-axis 154. The illustrated adapter 100 includes an adjustable horizontal clamp 130 configured to allow the anterior adapter portion body 132 to move horizontally (along the x-axis 154) to align the optical axis 150 of the camera 134 of the hand held computer device 102 with the optical axis of the adapter 100. The anterior adapter portion body 132 can be secured relative to the horizontal clamp 130 by a locking mechanism 136, such as the illustrated adjustable screw. The illustrated adapter 100 includes a third engagement surface or vertical contact point 138, illustrated with a hook type configuration to hold the hand held computer device 100 flush with the anterior adapter portion 104. The a third engagement surface 138 can hold the hand computer device 100 flush with the anterior adapter portion 104 while still allowing the anterior adapter portion body 132 to move or slide horizontally relative to the adjustable horizontal clamp 130. The dimensions and length of the third engagement surface 138 can be modified to accommodate different hand held computer device locations (see FIGS. 25A and 25B). For example, a longer hook could be used to accommodate a hand held computer device with a camera closer to the middle of the y-axis 156 of the hand held computer device. The adjustable horizontal clamp 130 can be spring loaded or use another mechanism to securely contact the hand held computer device 100. The adjustable grip can be configured to securely engage the hand held computer device edges by applying a compressive force between the two contact points where the adjustable horizontal grip engages with the hand held computer device. The adjustable grip can be sized to accommodate hand held computer devices having various widths.

The adjustable horizontal clamp 130 can allow the macro lens 140 and light source 142 to be aligned with optical axis 150 of the hand held computer camera 134. Different hand held computer devices have different dimensions and different cameras positions. For example, the iPhone 6 is in the left corner, many android phones are centrally located and further away from the edge, HTC phones are located in the right corner, etc. The anterior body can be adjusted relative to the adjustable horizontal clamp 130 to align the camera 134 with the lenses 110, 140.

Figure 6:
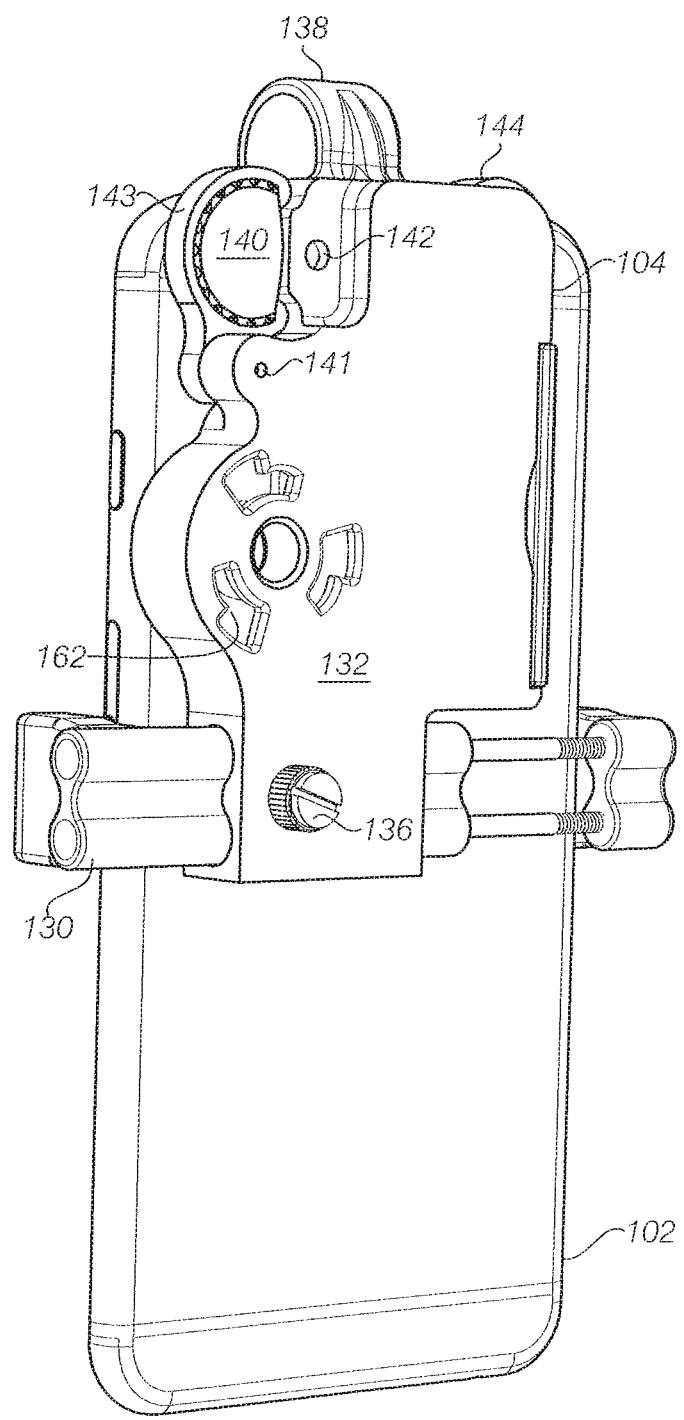
FIG. 6 is a front view of an anterior portion of an adapter attached to a hand held computer device in accordance with some embodiments.
Figure 7:
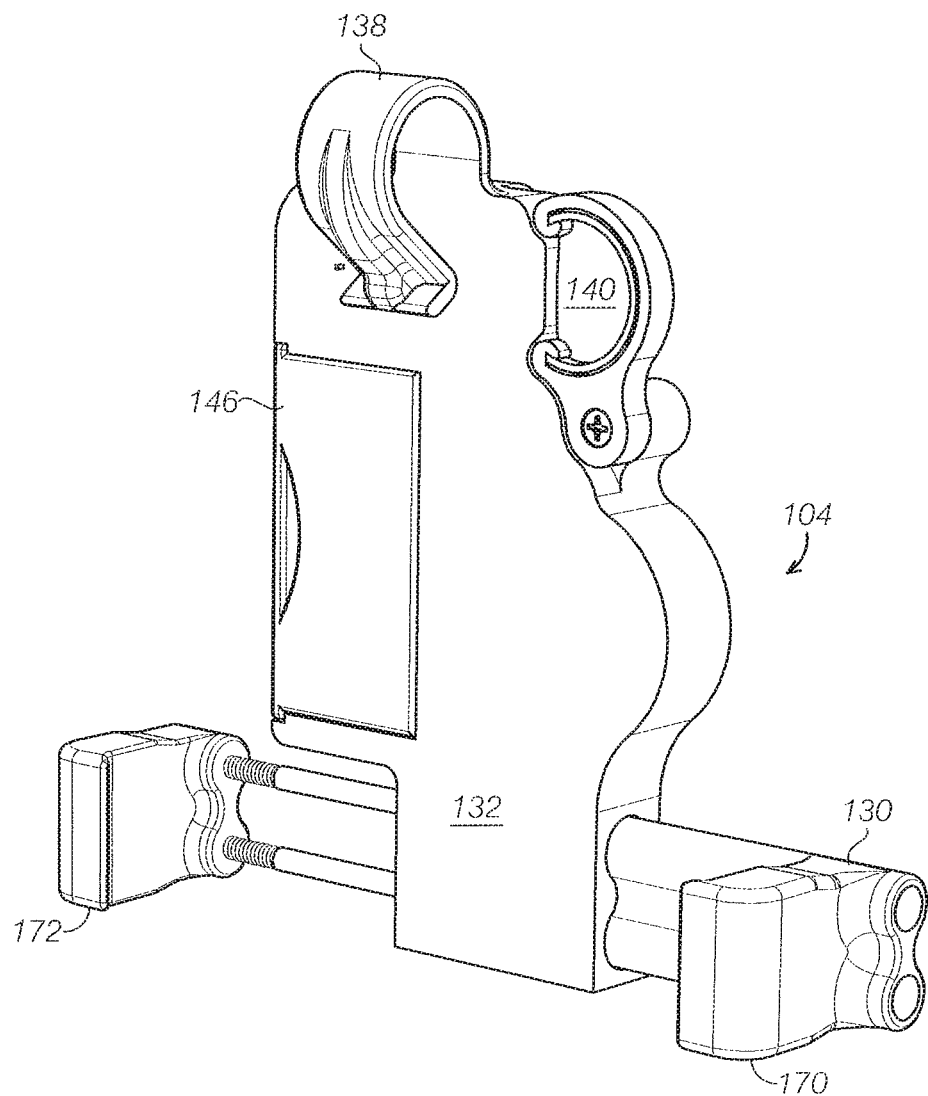
FIG. 7 is a back view of an anterior portion of an adapter in accordance with some embodiments.
Figure 8:
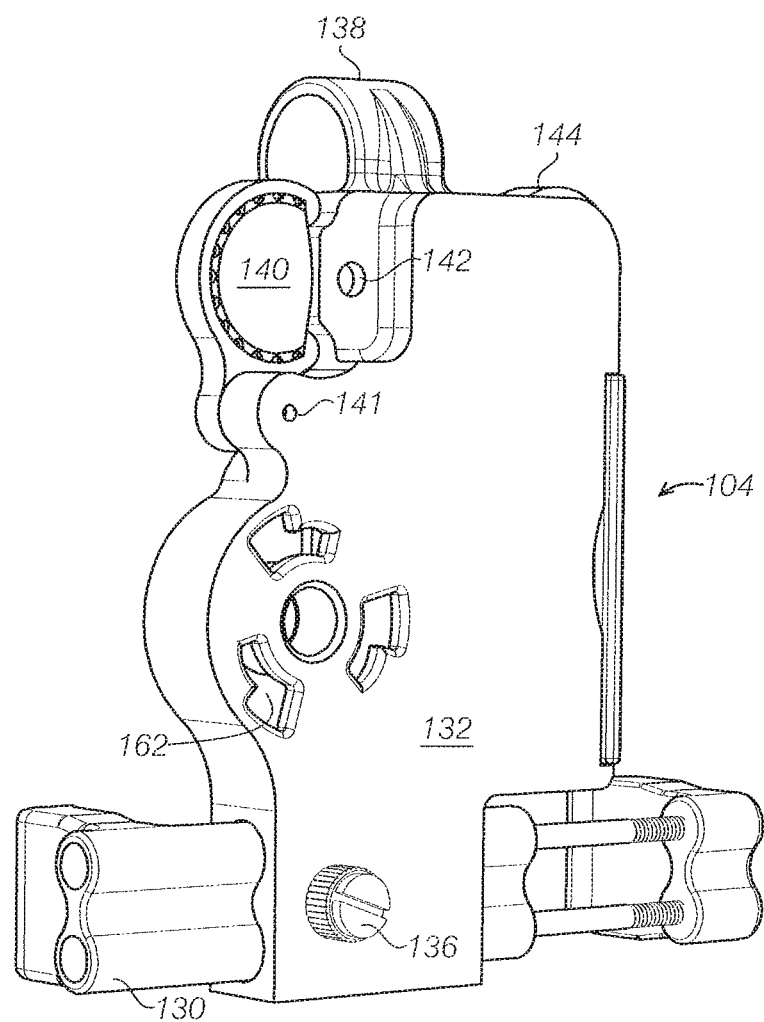
FIG. 8 is a front view of an anterior portion of an adapter attached to a hand held computer device in accordance with some embodiments.

The illustrated anterior adapter portion 104 also includes a macro lens 140, macro lens holder 143, and lens holder hinge 141, light source 142, and light source dial control 144. The illustrated light source 142 is a LED. The lens holder 143 can be adapted to receive other types of lenses. The lens 140 and lens holder 143 can rotate about the lens holder hinge 141 to move the macro lens 140 between a position in the optical axis 150 of the camera and a second position outside of the optical axis of the camera 150. FIG. 1 shows the macro lens 140 and lens holder 143 at a position outside of the optical axis 150 of the camera. FIG. 6 shows the macro lens 140 in the optical axis of the camera 150. The light source 142 can be controlled by the light source control 144, which is illustrated as a rotatable knob or dial. The light source 142 can also include one or more optional light diffuser elements. The optional light diffuser elements can be within the housing and in front of the light source 142.

Figure 2:
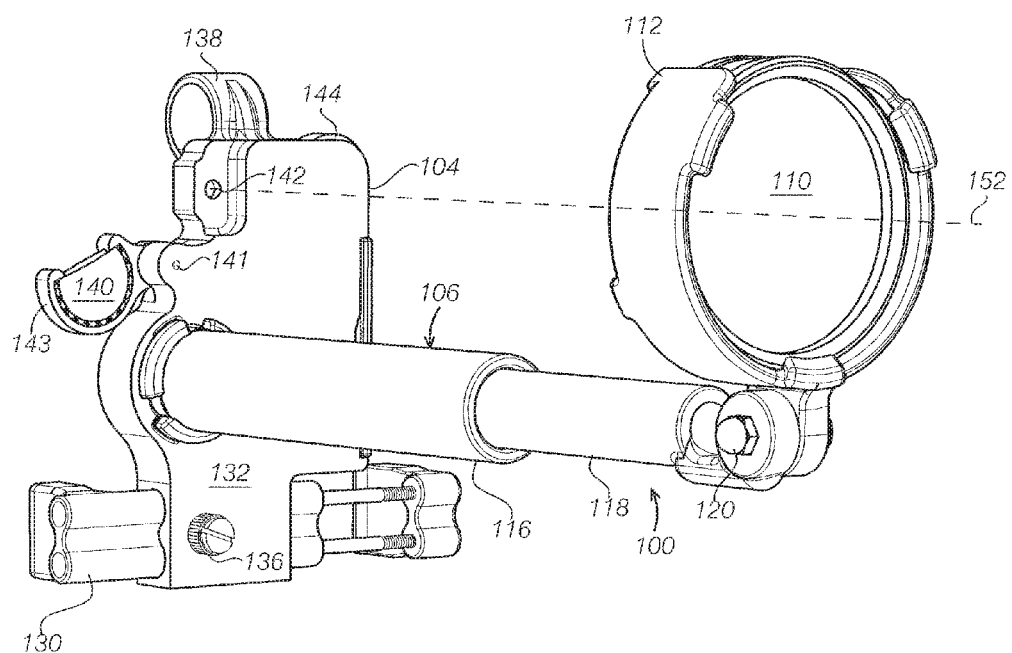
FIG. 2 is a front view of an adapter in accordance with some embodiments.
Figure 3:
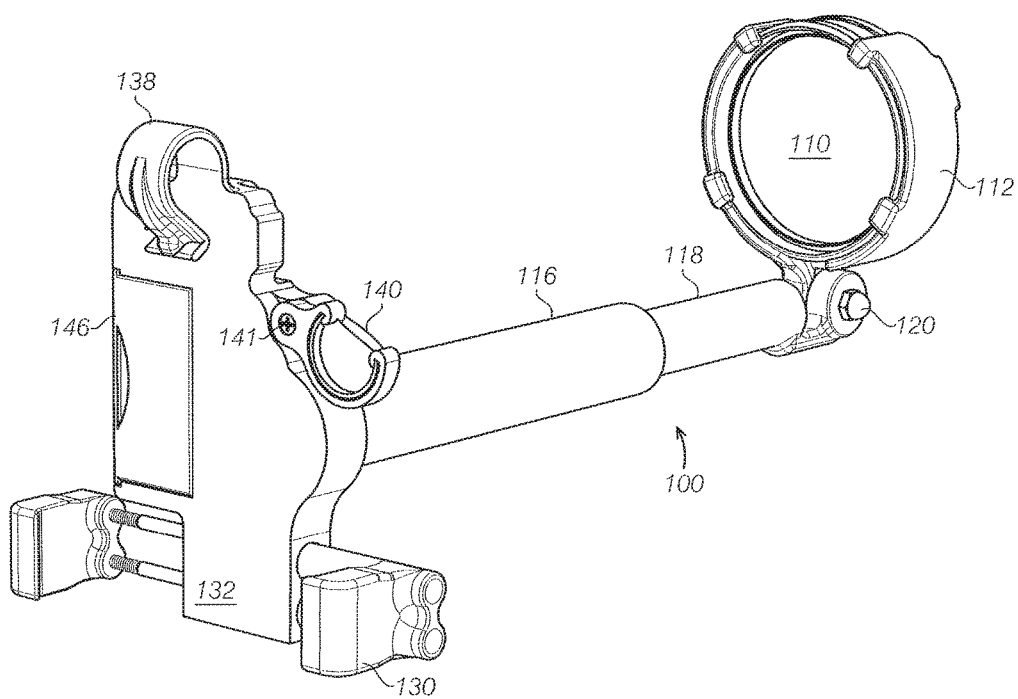
FIG. 3 is a back view of an adapter in accordance with some embodiments.
Figure 4:
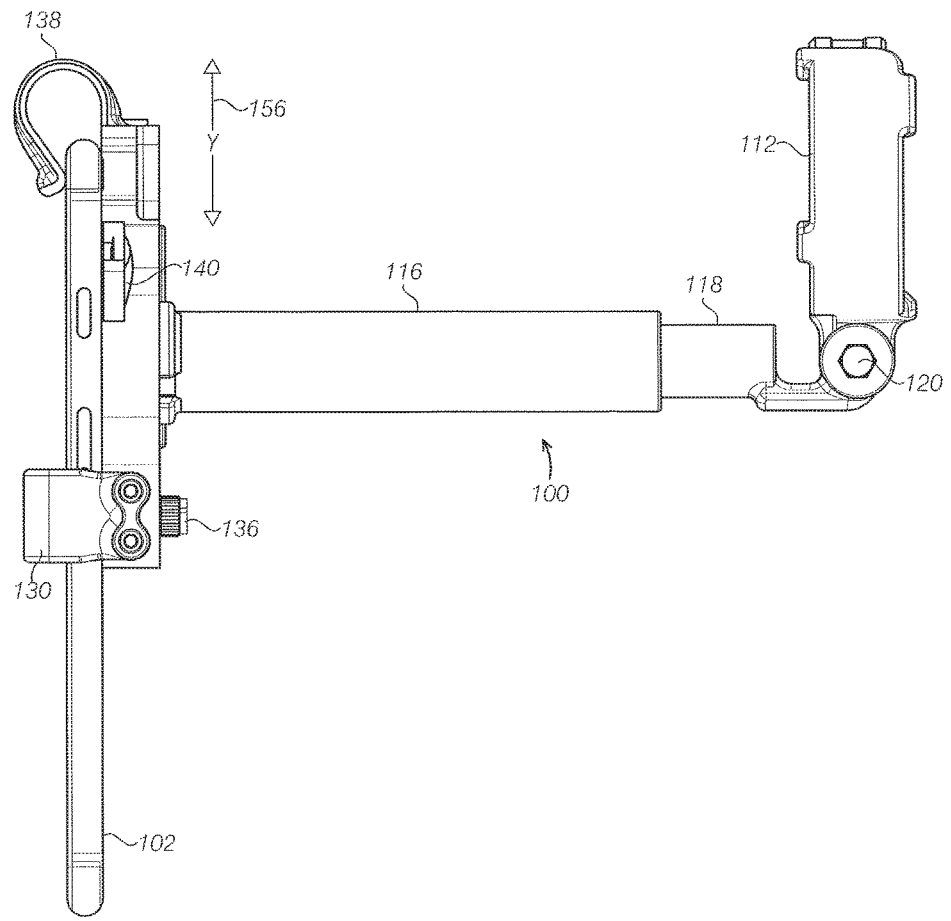
FIG. 4 is a side view of an adapter in accordance with some embodiments.

FIG. 2 is a front view and FIG. 3 is a back view of the adapter 100 of FIG. 1 without a hand held computer device 102. The adjustable light source 142 has an optical axis or pathway 152. The anterior adapter portion body 132 includes a battery compartment 146 configured to receive a power source, such as a battery. FIG. 4 is a side view of an adapter in accordance with some embodiments.

FIG. 5 illustrates the anterior adapter portion 104 and posterior portion 106 of the adapter 100 separate from one another. The posterior portion 106 is illustrated with the lens holder 112 in a folded position relative to the telescoping section 118. The posterior portion 106 includes a male engagement structure 160 configured to be received within a complementary mating structure 162 on the anterior adapter portion body 132. The illustrated engagement structures 160, 162 are configured to lock in place by turning the surfaces relative to one another. The ability to disengage the posterior portion 106 from the anterior adapter portion 104 can improve the portability and storage of the device while also decreasing the likelihood of the posterior portion being damaged. The adjustable screw 120 can be adjusted to fold the lens holder 112 as shown in FIG. 5. The adjustable screw 120 can also be adjusted to retract the telescoping shaft 118 relative to the base shaft 116 as shown in FIG. 5.

The axial length between the camera 134 and the lens 110 can be adjusted by moving the telescoping shaft 118 relative to the base shaft 116 to achieve the desired distance. The axial length can be adjusted until the camera 134 can record a desired image of the retina. The horizontal position along the x-axis 154 of the anterior adapter portion body 132 to line the optical axis 150 of the camera 134 with the lens 110.

Figure 9:
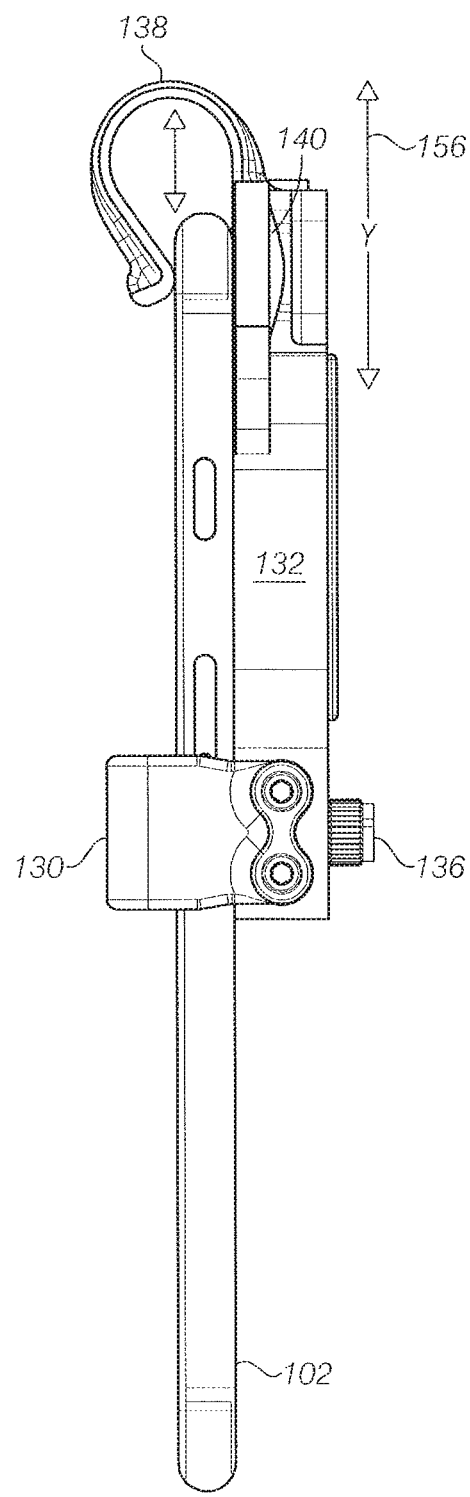
FIG. 9 is a side view of an anterior portion of an adapter attached to a hand held computer device in accordance with some embodiments.

FIGS. 6-9 illustrate various views of the anterior adapter portion 104 of the adapter 100. The adapter 100 can be securely held to the hand held computer device 102 by the three-point connection between the anterior adapter portion 104 and the hand held computer device 102. The adjustable horizontal clamp 130 can be spring loaded to securely clamp on to the hand held computer device 102 with the first clamp surface 170 and second clamp surface 172. Moving the anterior adapter portion body 132 relative the adjustable horizontal clamp 130 allows for the optimal positioning of the lens 140 and light source 142 relative to the camera 134. FIG. 9 shows how the third engagement surface 138 can move along the y-axis 156 to accommodate different hand held computer device camera locations.

Figure 10:
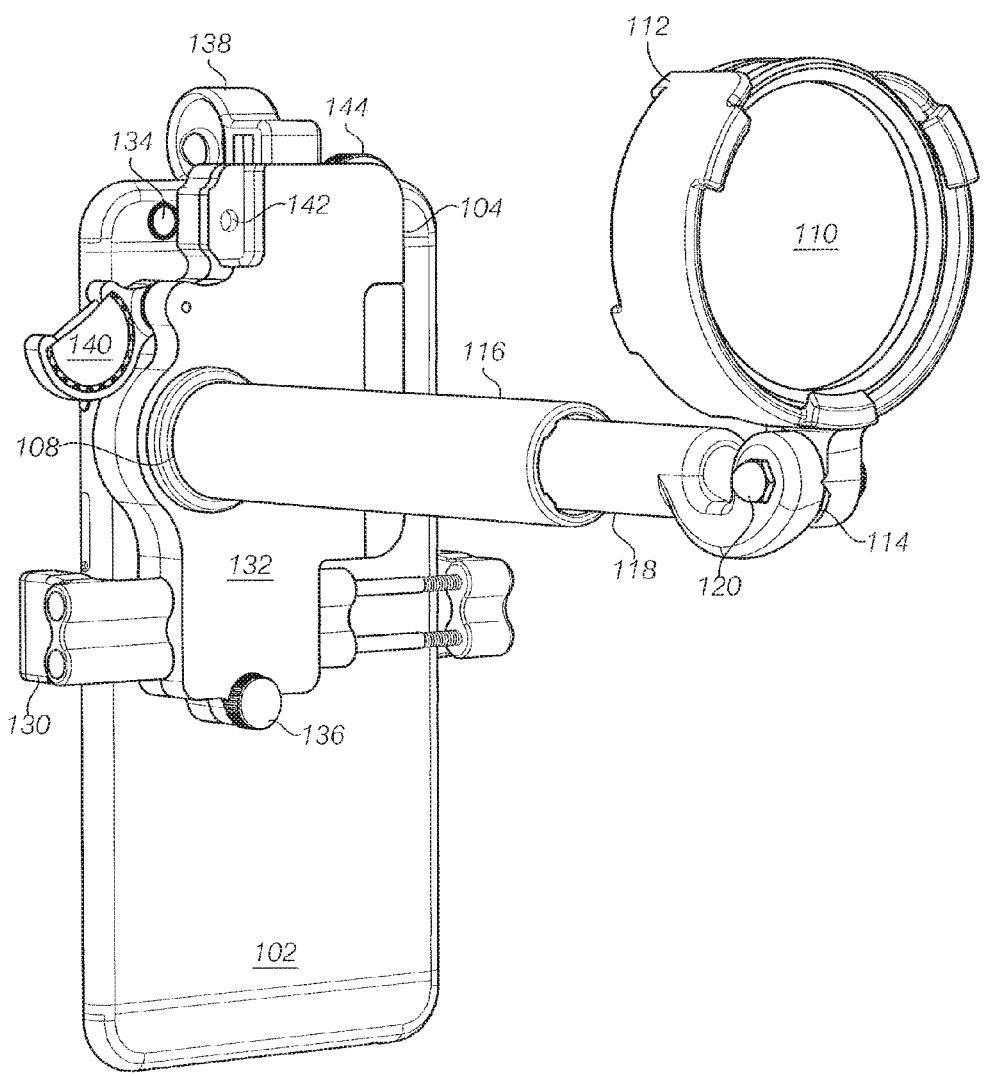
FIG. 10 is a front view of an adapter attached to a hand held computer device in accordance with some embodiments.
Figure 11:
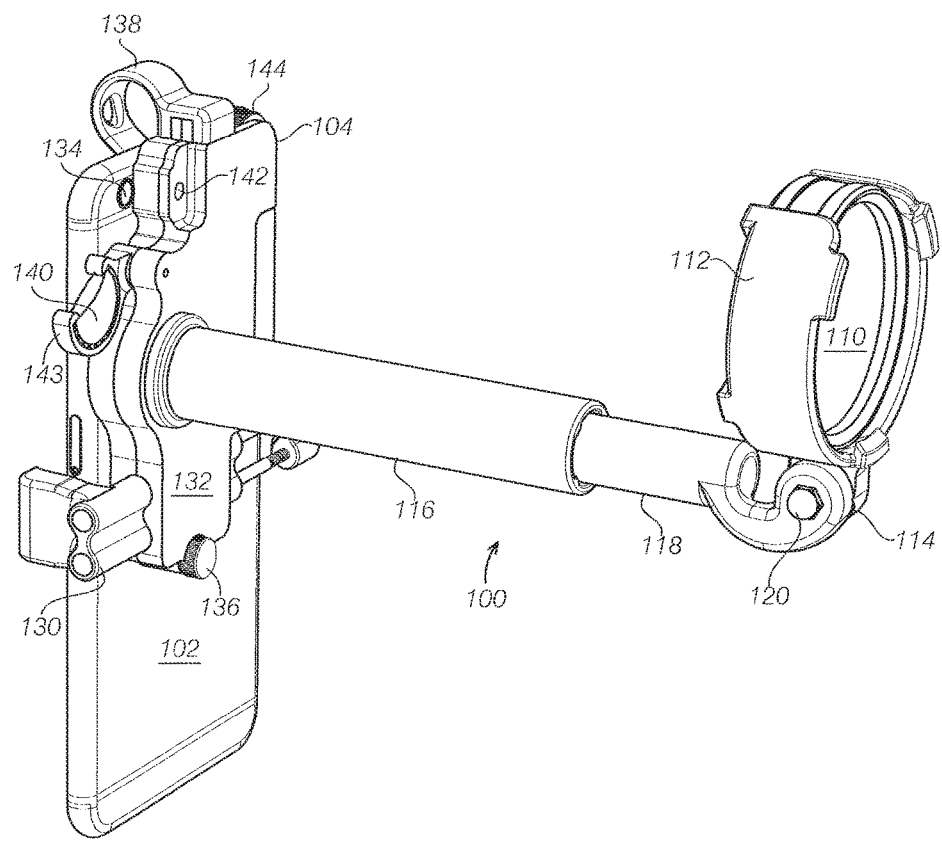
FIG. 11 is another front view of an adapter attached to a hand held computer device in accordance with some embodiments.

FIGS. 10-11 illustrate front views of the adapter attached to the hand held computer device with the macro lens 140 out of the optical axis 150 of the camera 134. The length of the telescoping section is shorter in FIGS. 10-11 versus the configuration illustrated in FIG. 1.

Figure 12:
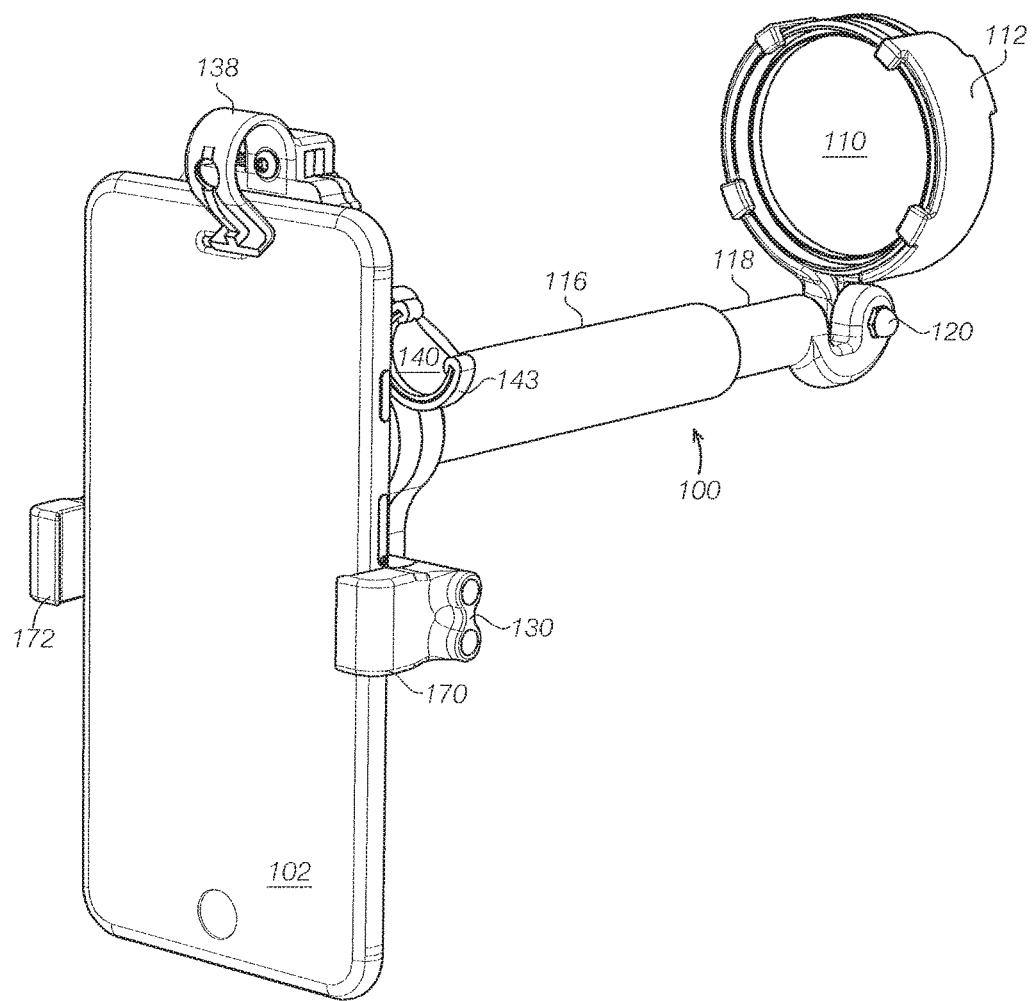
FIG. 12 is a back view of an adapter attached to a hand held computer device in accordance with some embodiments.
Figure 13:
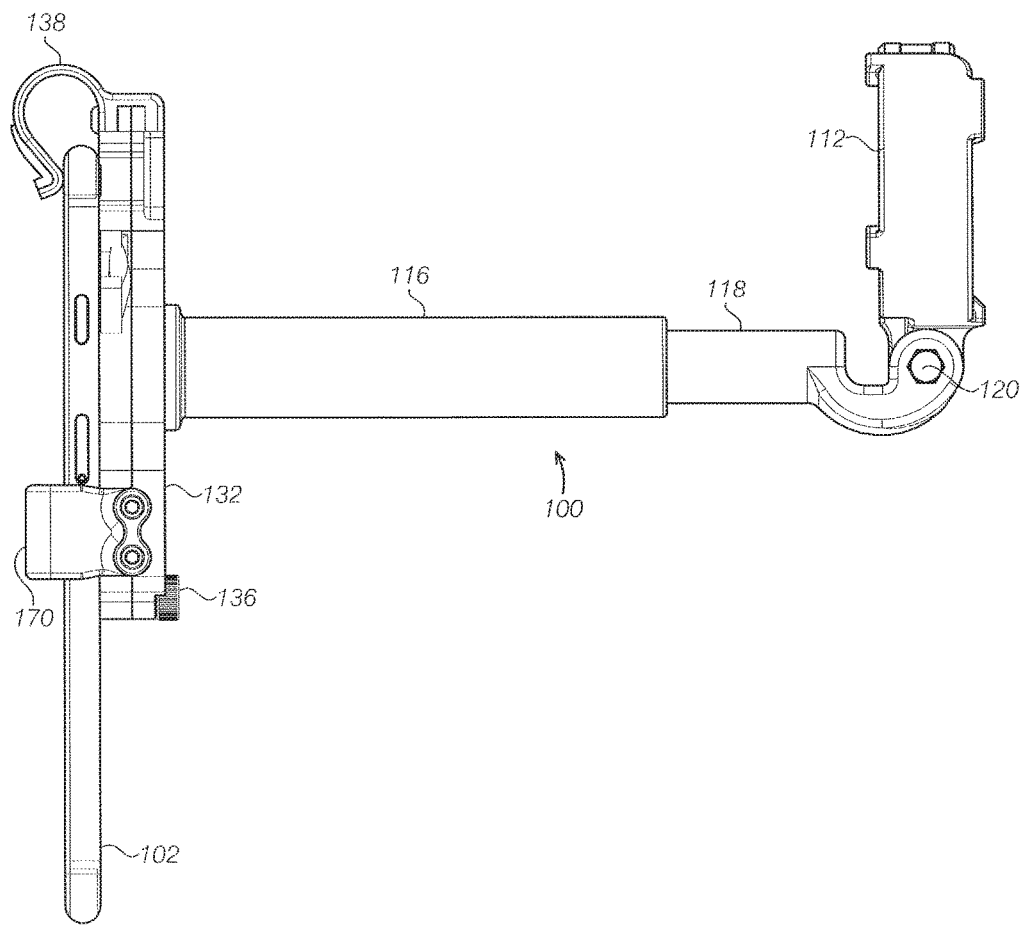
FIG. 13 is a side view of an adapter attached to a hand held computer device in accordance with some embodiments.

FIG. 12 is a back view of an adapter attached to a hand held computer device 102 in accordance with some embodiments. The display side of the hand held computer device 102 is shown in FIG. 12. FIG. 13 is a side view of an adapter 100.

Figure 14:
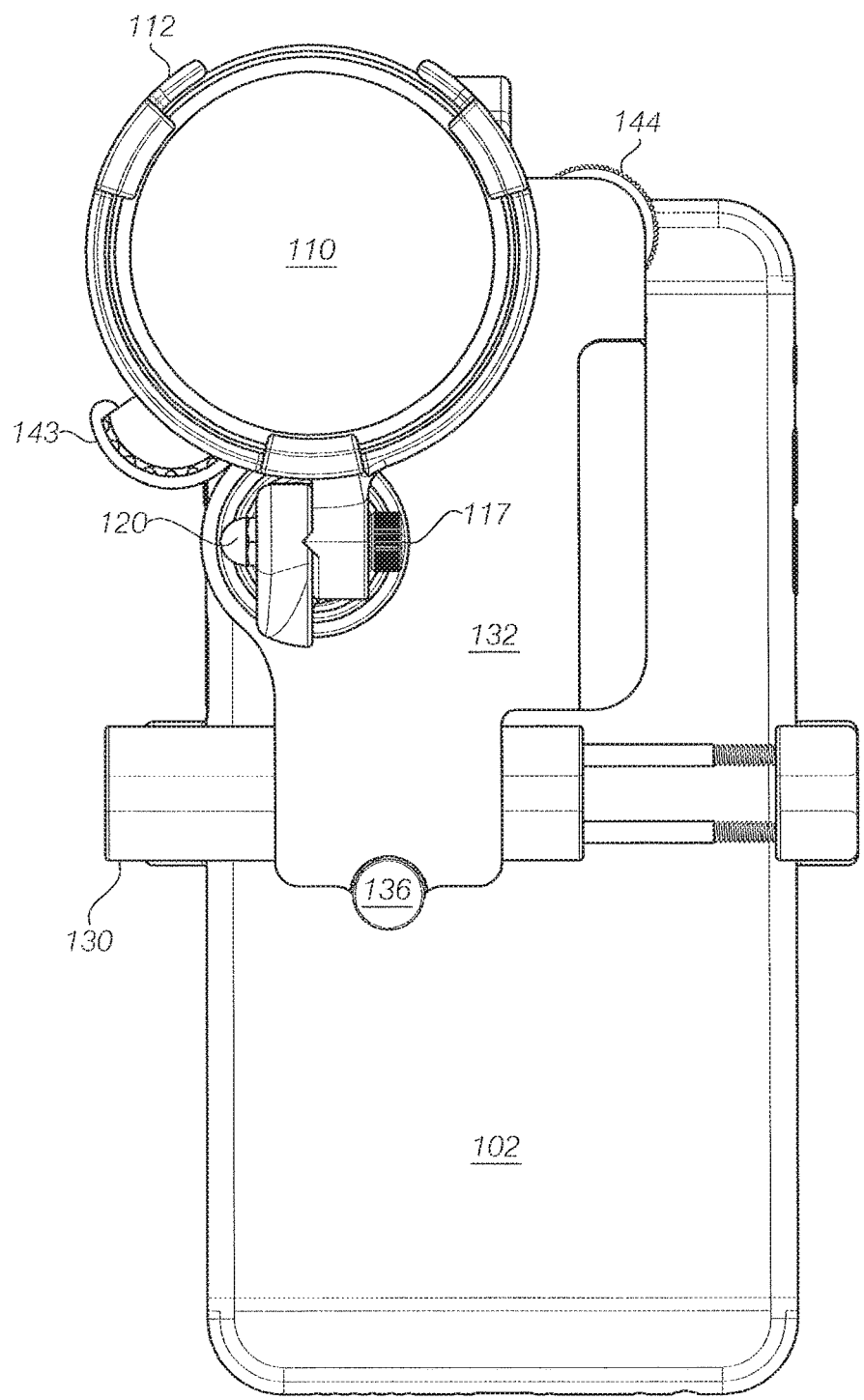
FIG. 14 is a front view of an adapter attached to a hand held computer device in accordance with some embodiments.
Figure 15:
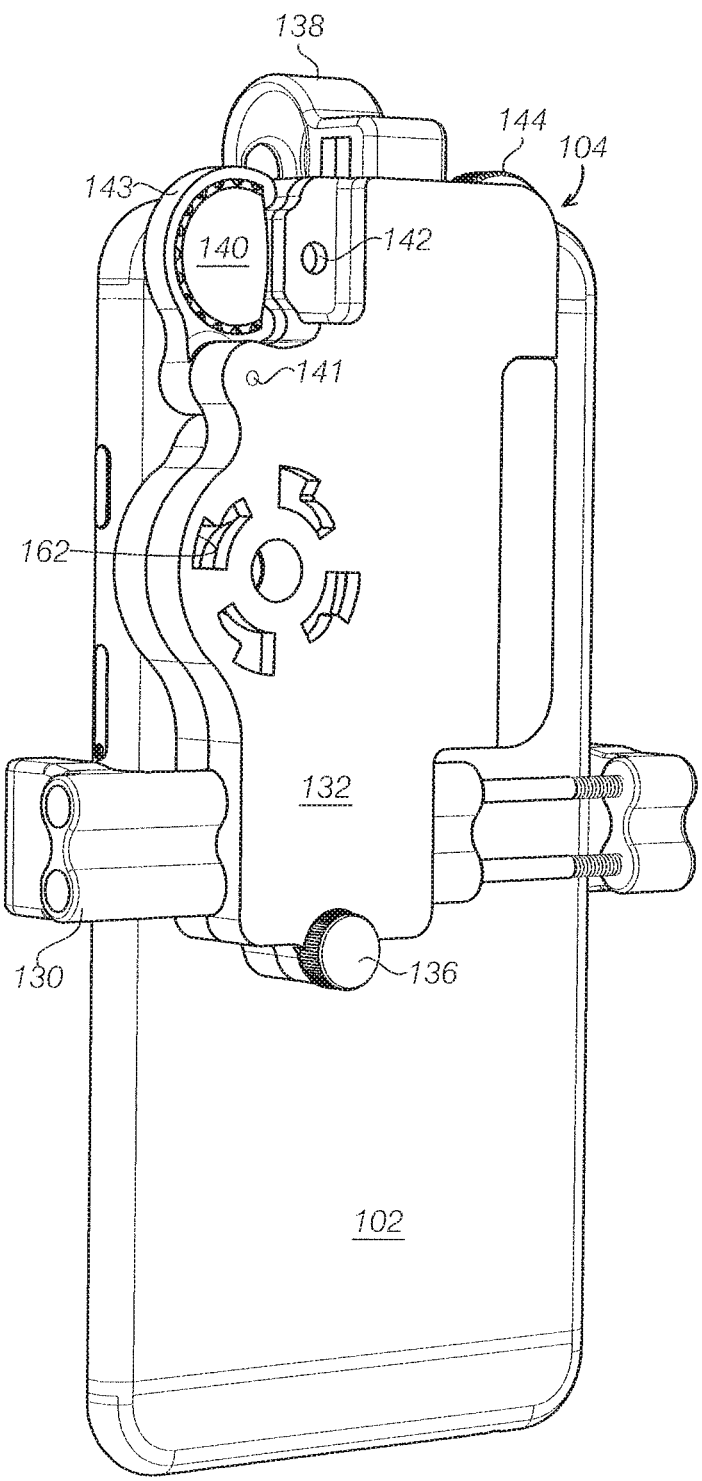
FIGS. 15 and 16 are front views of an anterior portion of an adapter engaged with a hand held computer device with a macro lens in the optical pathway of the camera of the hand held computer device in accordance with some embodiments.
Figure 16:
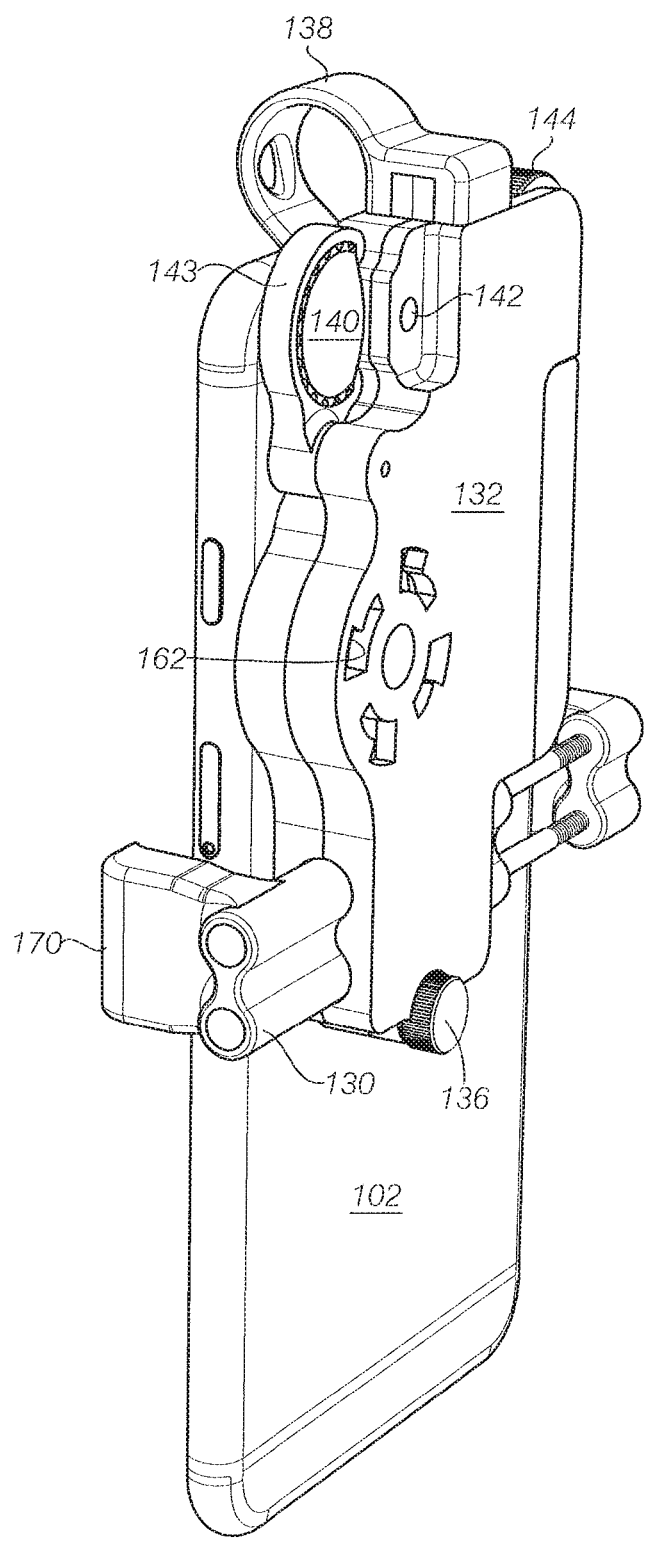
Figure 17:
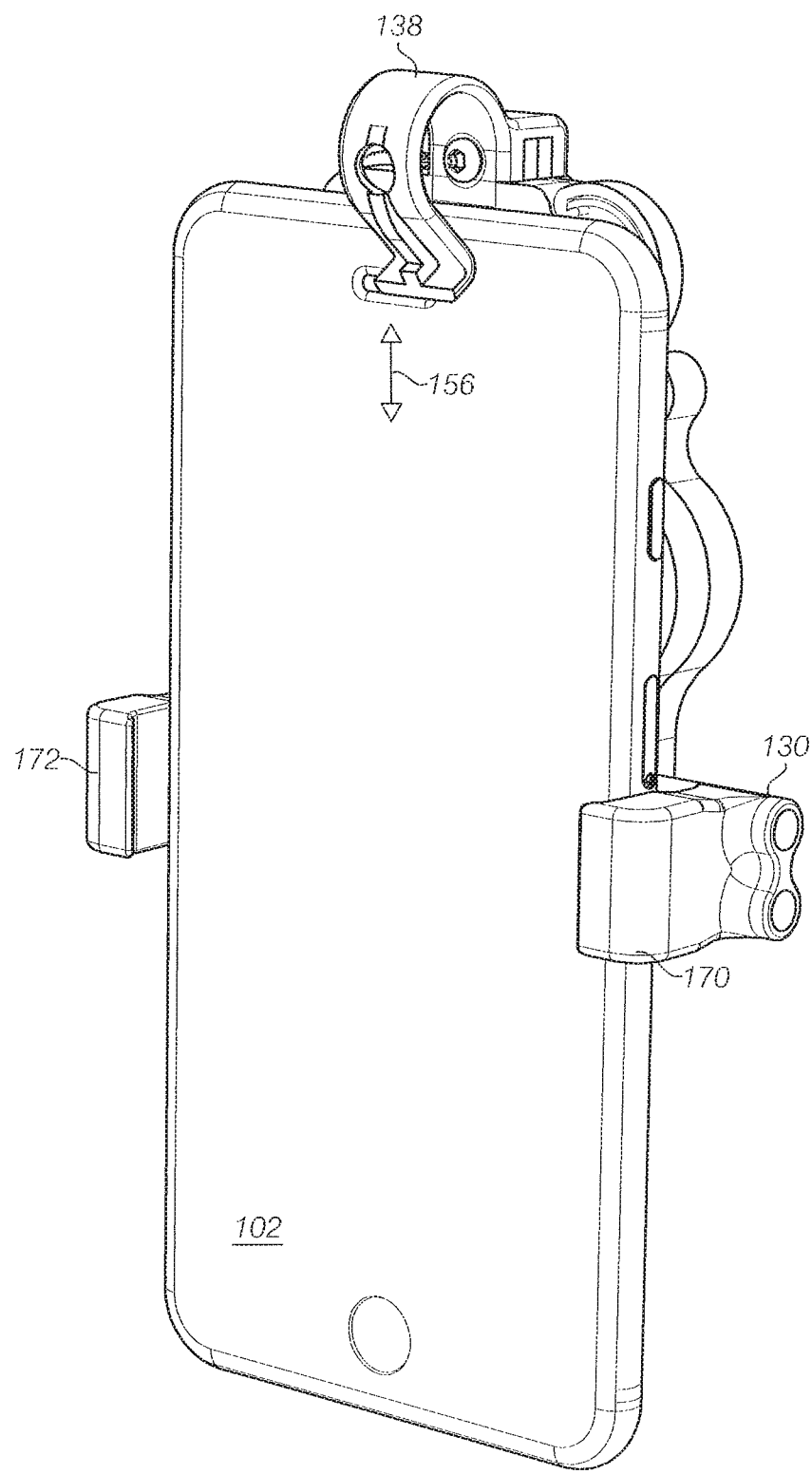
FIGS. 17, 18 and 19 are back, side, and head on views of an anterior portion of an adapter engaged with a hand held computer device with a macro lens in the optical pathway of the camera of the hand held computer device in accordance with some embodiments.
Figure 18:
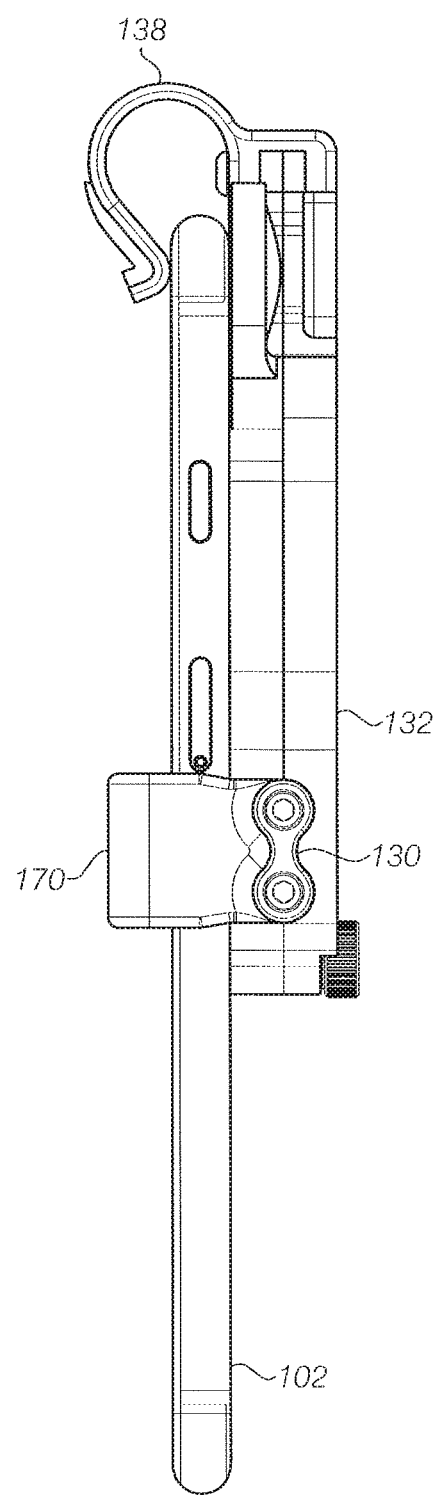
Figure 19:
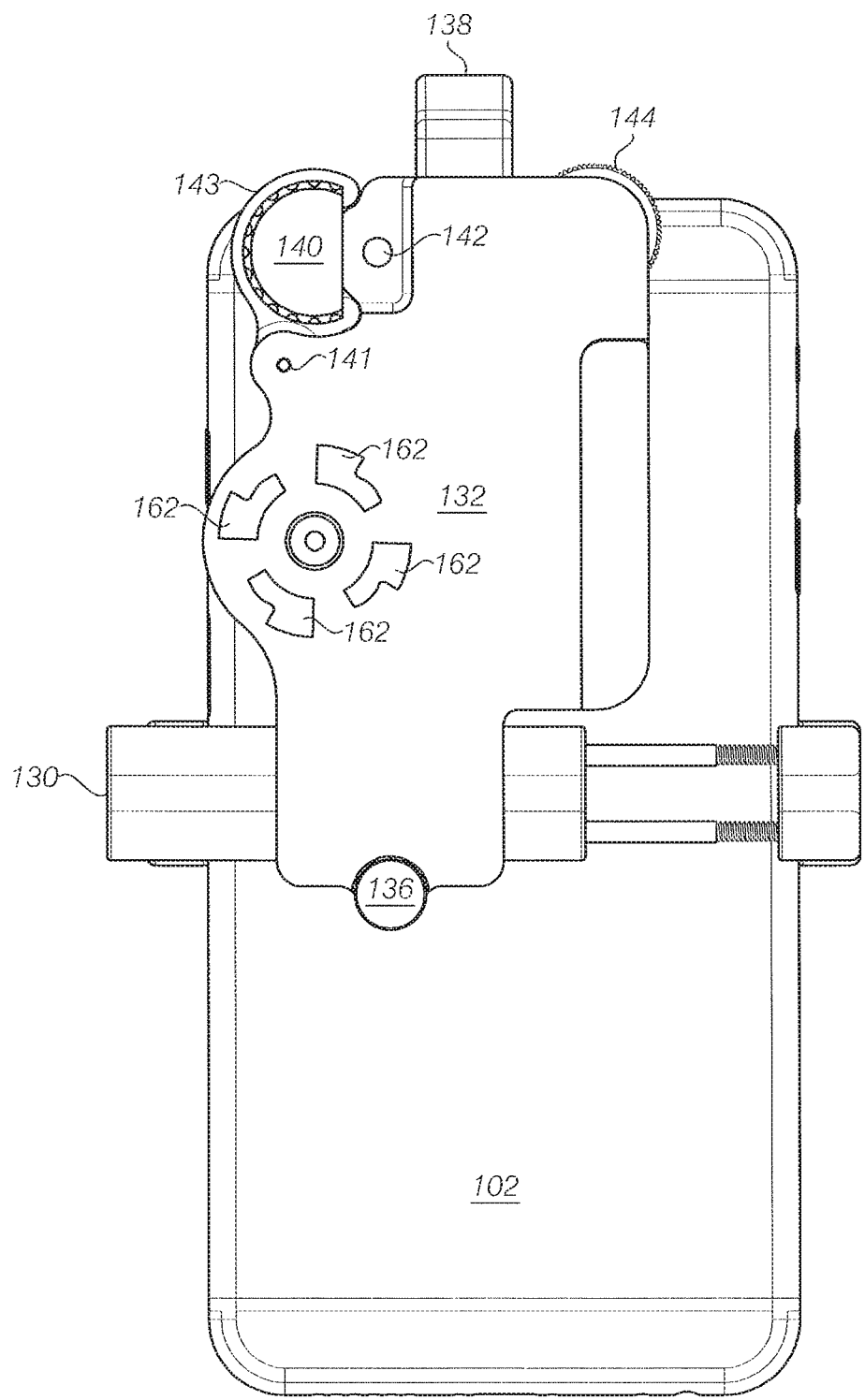
Figure 20:
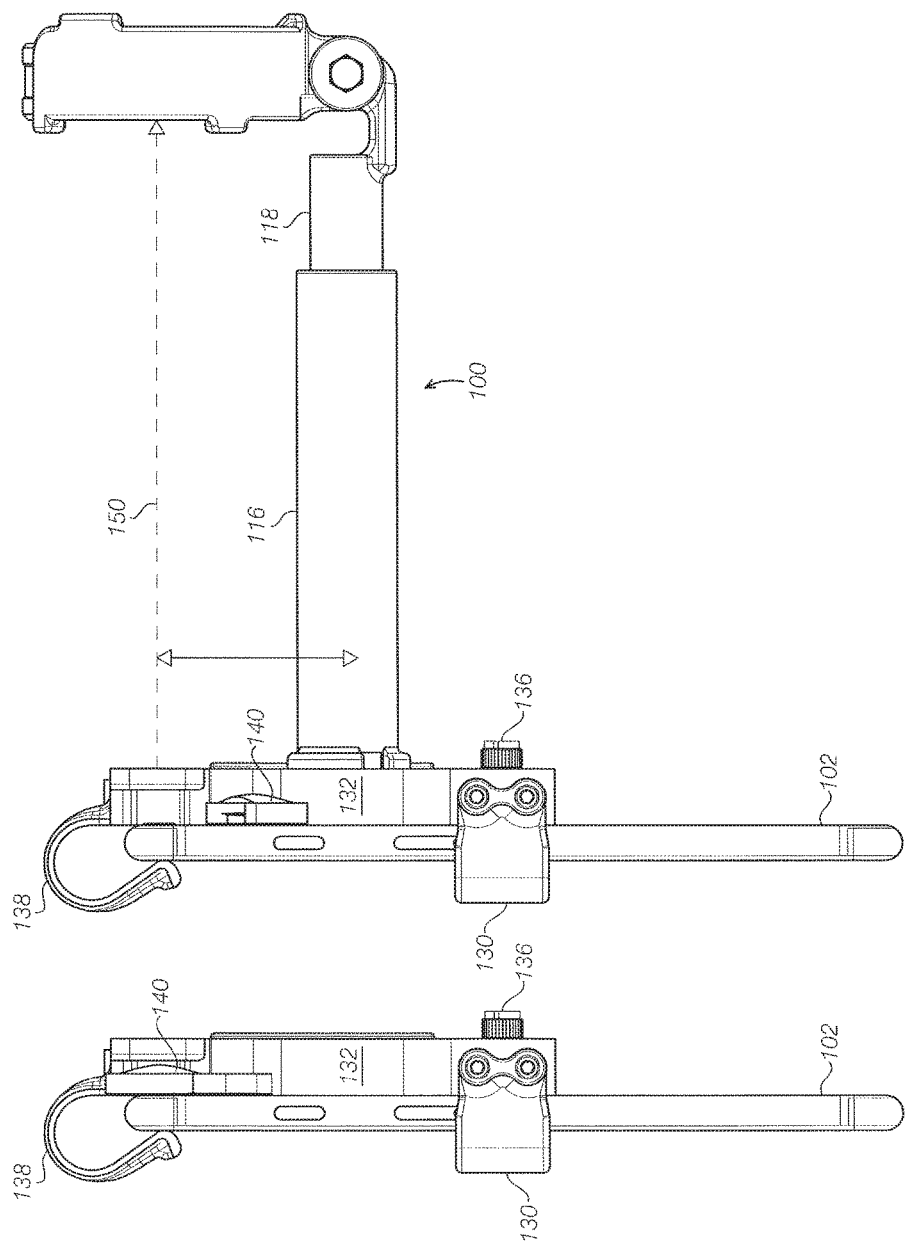
FIG. 20A illustrates a side view of an anterior portion of an adapter engaged with a hand held computer device with a macro lens in the optical pathway of the camera of the hand held computer device in accordance with some embodiments.
FIG. 20B illustrates a side view of an anterior portion and posterior portion of an adapter engaged with a hand held computer device with a macro lens out of the optical pathway of the camera of the hand held computer device in accordance with some embodiments.
Figure 21:
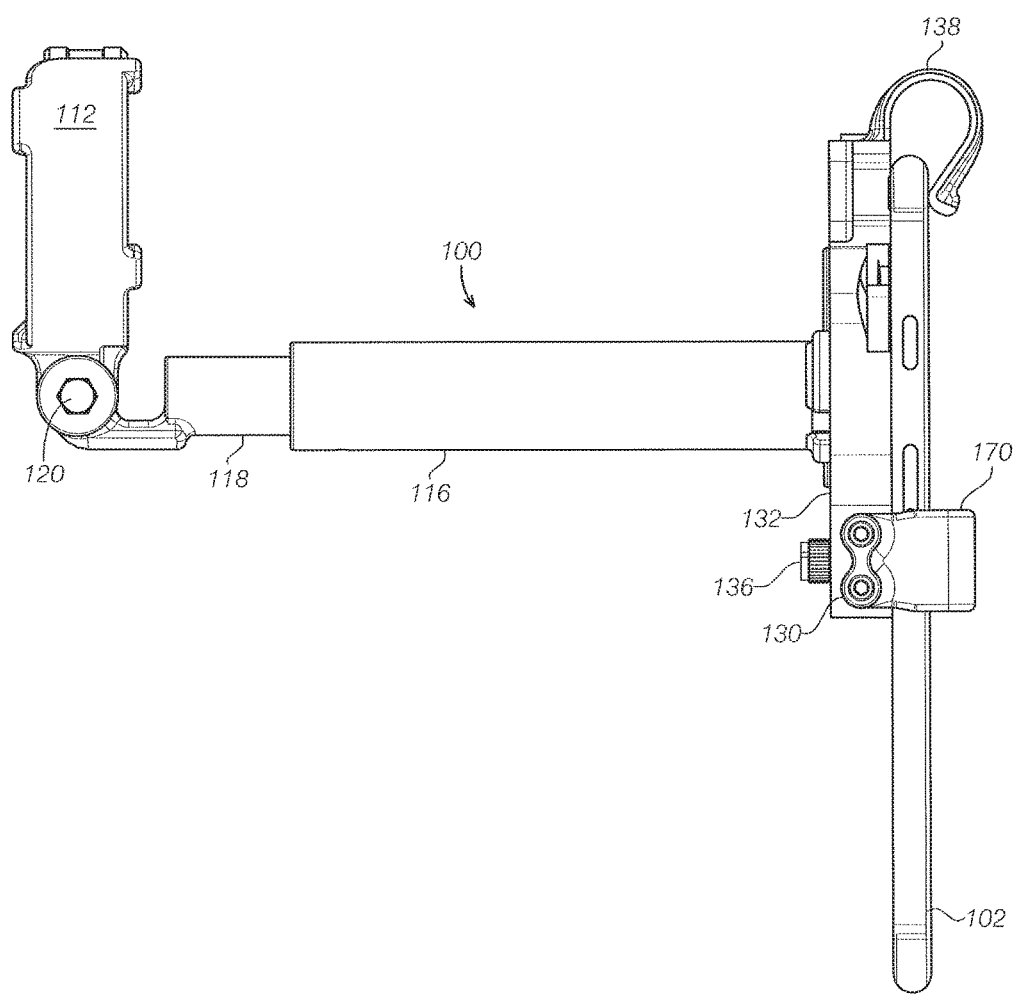
FIG. 21 illustrates a side view of an anterior portion and posterior portion of an adapter engaged with a hand held computer device with a macro lens out of the optical pathway of the camera of the hand held computer device in accordance with some embodiments.

FIG. 14 is a front view of an adapter attached to a hand held computer device 102 in accordance with some embodiments. FIG. 14 shows the telescoping section locking mechanism 117 that can be used to secure the relative movement between the base section 116 and telescoping section 118 of the posterior portion 106. The dial 144 is adapted to adjust and control the intensity of the light source. FIGS. 15-21 illustrate additional views of the adapter 100.

Figure 22A:
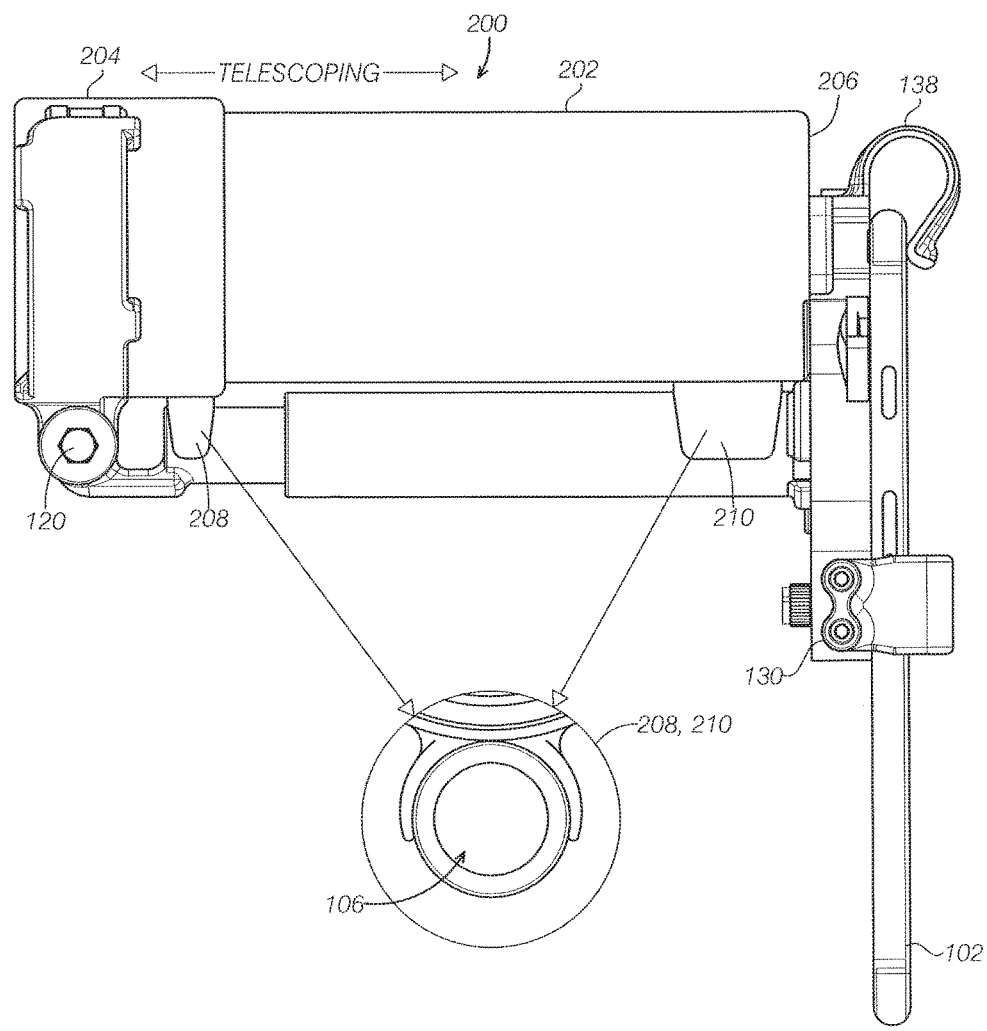
FIG. 22 illustrates a side view of an adapter engaged with a hand held computer device and optical pathway enclosure adapter in accordance with some embodiments.
Figure 23:
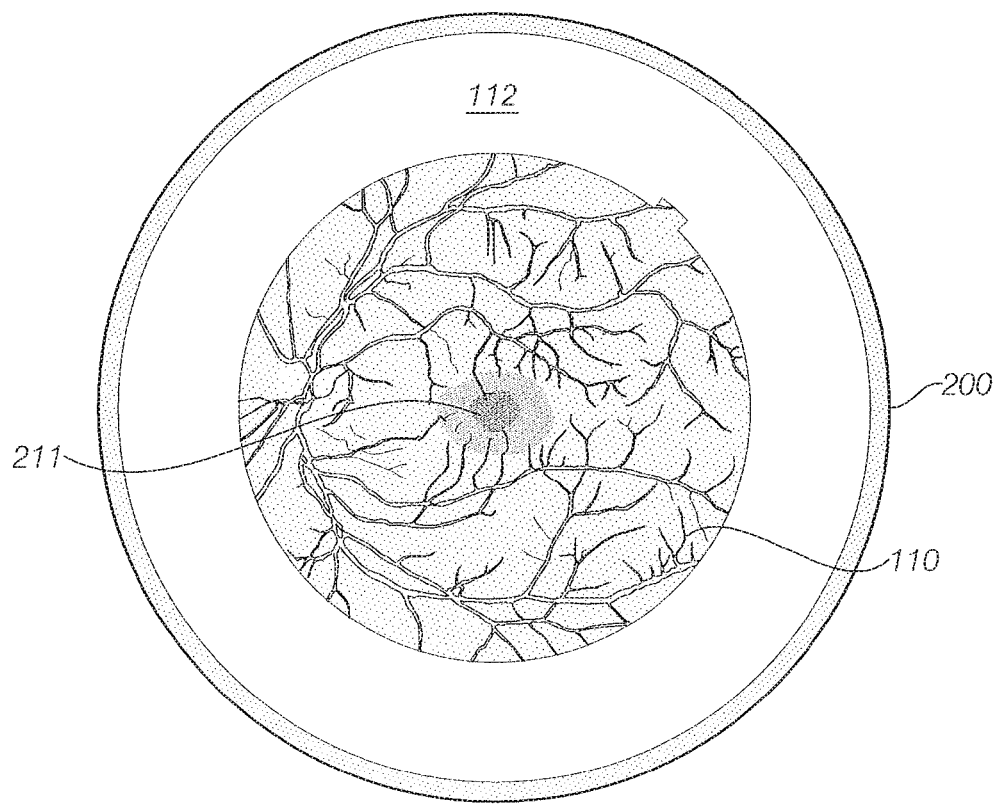
FIG. 23 is an example of a cross-sectional view through the optical pathway enclosure in accordance with some embodiments.

FIG. 22 illustrates a side view of an adapter engaged with a hand held computer device 102 and optional, reversibly attached optical pathway enclosure 200 in accordance with some embodiments. The enclosure adapter 200 includes a first portion 202 and second portion 204 configured to move relative to one another to move with the telescoping section of the posterior portion. The enclosure adapter 200 includes a first clamp 208 and second clamp 210 configured to engage with the telescoping portion and base portion of the adapter. The enclosure adapter 200 includes a back portion 206 configured to engage with the camera 134 of the hand held computer device. The enclosure adapter 200 can block out exterior light to improve the quality of the images captured using the posterior portion. FIG. 23 illustrates an exemplary cross-sectional view that can be produced by the adapters described herein. The cross-sectional view shows the enclosure adapter 200, ophthalmoscopy lens 110, lens holder 112, and retina 211. An image of the retina 211 can be captured by the camera 134.

Figure 24A:
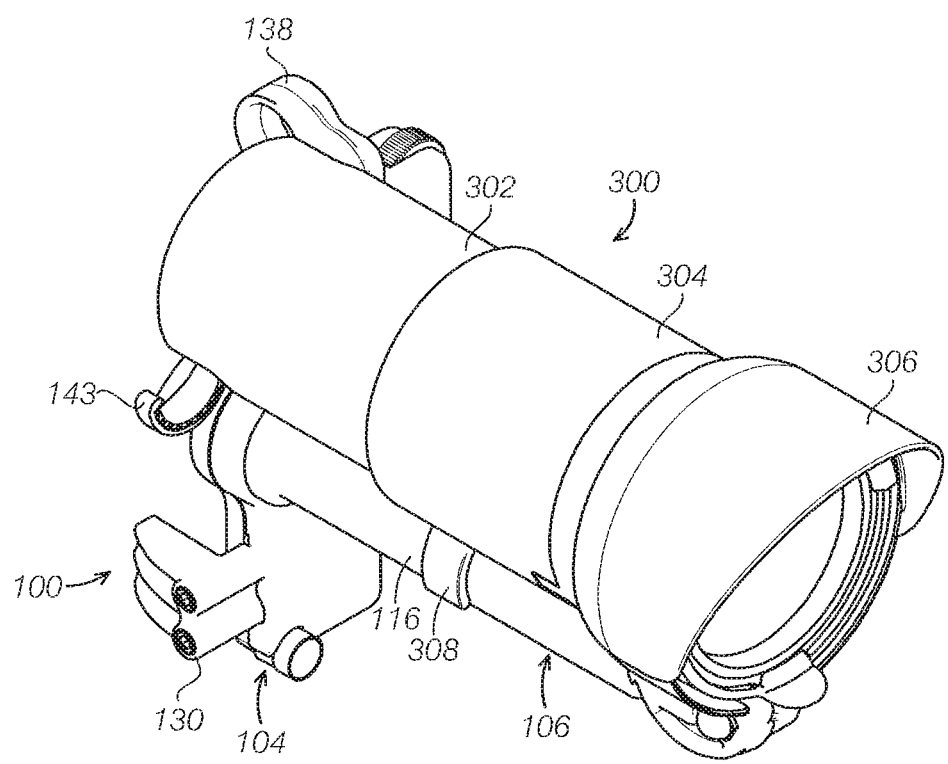
FIGS. 24A and 24B illustrate an optical pathway enclosure adapter engaged with an adapter in accordance with some embodiments.
Figure 24B:
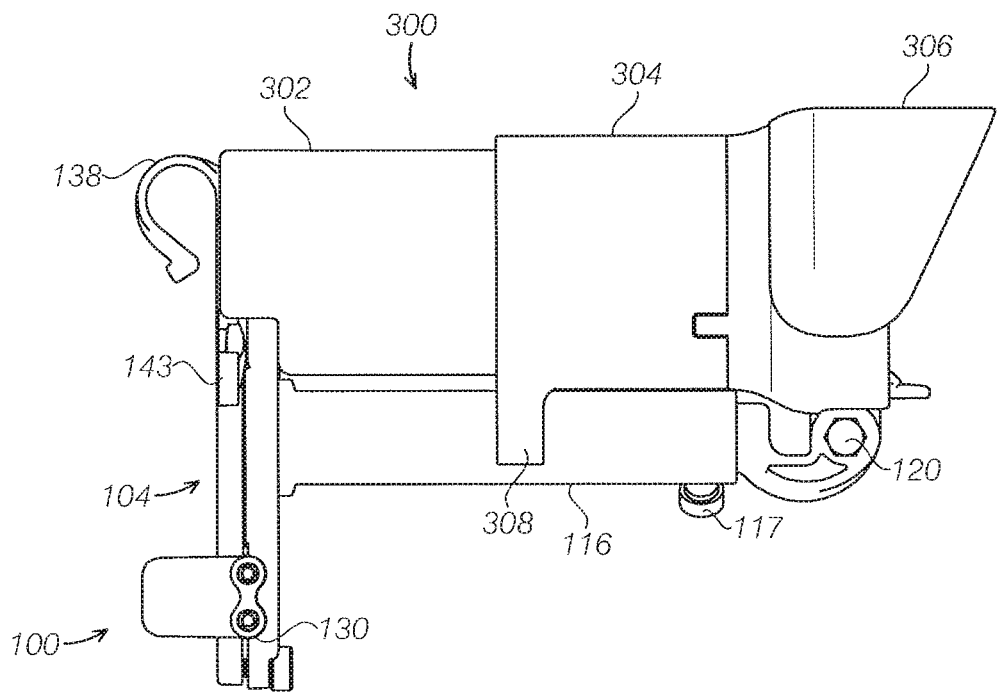
Figure 24C:
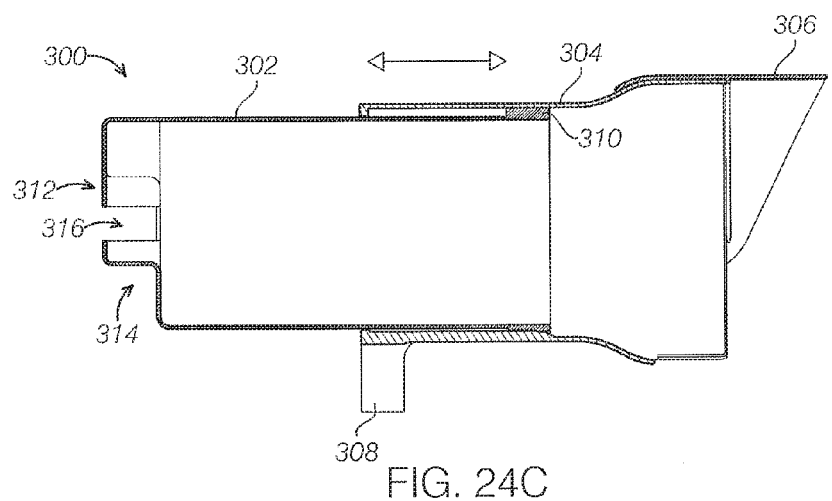
FIGS. 24C and 24D are cross-sectional and exploded views of an optical pathway enclosure adapter in accordance with some embodiments.
Figure 24D:
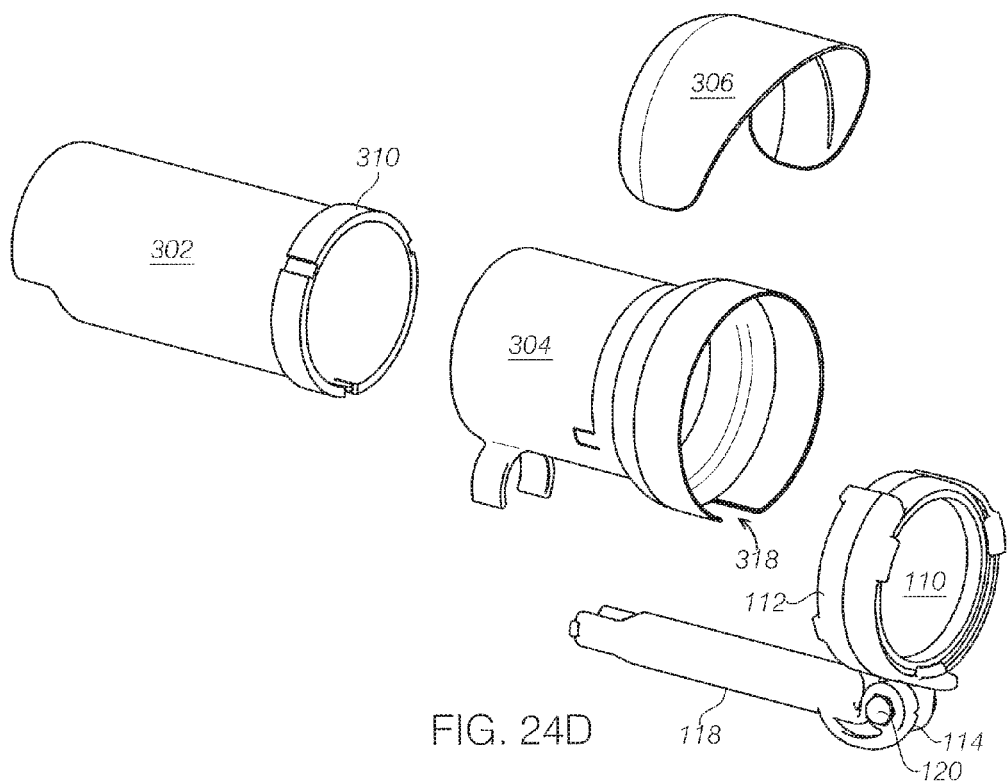

FIGS. 24A and 24B illustrate views of an optical pathway enclosure adapter 300 engaged with an adapter 100 in accordance with some embodiments. FIGS. 24C and 24D are cross-sectional and exploded views of an optical pathway enclosure adapter 300. The enclosure adapter 300 is configured for blocking exterior light from the optical pathway between the ophthalmoscopy lens 110 and the camera 134 of the hand held computer device. The enclosure adapter 300 includes a first portion 302 and second portion 304. An optional third portion 306 can be used to provide additional blocking of exterior light from the ophthalmoscopy lens 110. The enclosure adapter 300 includes a clip 308 for removably engaging with the telescoping section 118 and/or base section 116. The first portion 302 and second portion 304 can slide relative to one another so that the length of the first portion 302 and second portion 304 can be adjusted to match the length of the poster portion 106. The first portion 302 includes a stop 310 to limit axial movement between the first portion 302 and second portion 304. The first portion includes a back cover portion 312 with a hand held computer engagement surface 314 and an opening to accommodate the light source 142 and camera 134 of the hand held computer device. The second portion 304 includes a groove 318 to engage with and receive a portion of the lens holder 112 to hold the lens 110 within the second portion 304 of the enclosure 300. FIGS. 24A-24B illustrate the macro lens 140 and lens holder 143 out of the optical axis of the camera 134.

Figure 25A:
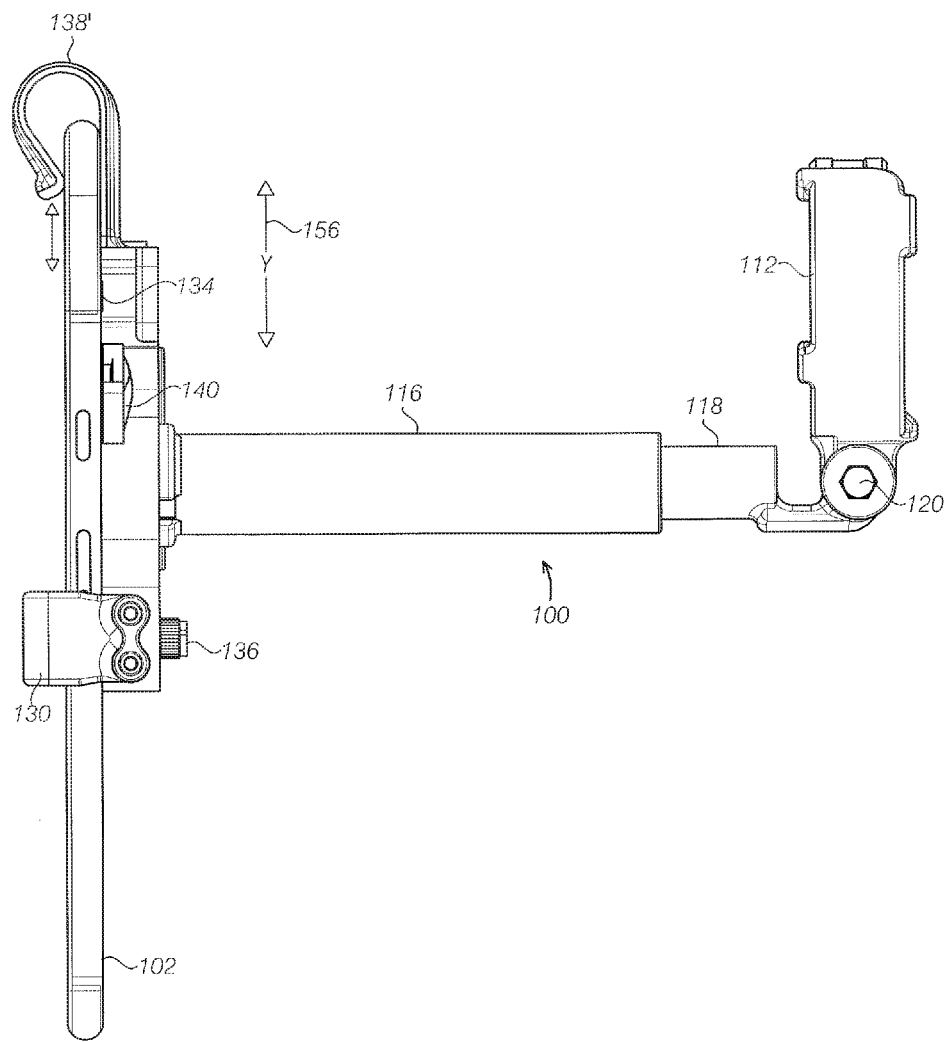
FIGS. 25A and 25B illustrate additional embodiments of an anterior adapter engaged with a hand held computer device in accordance with some embodiments.
Figure 25B:
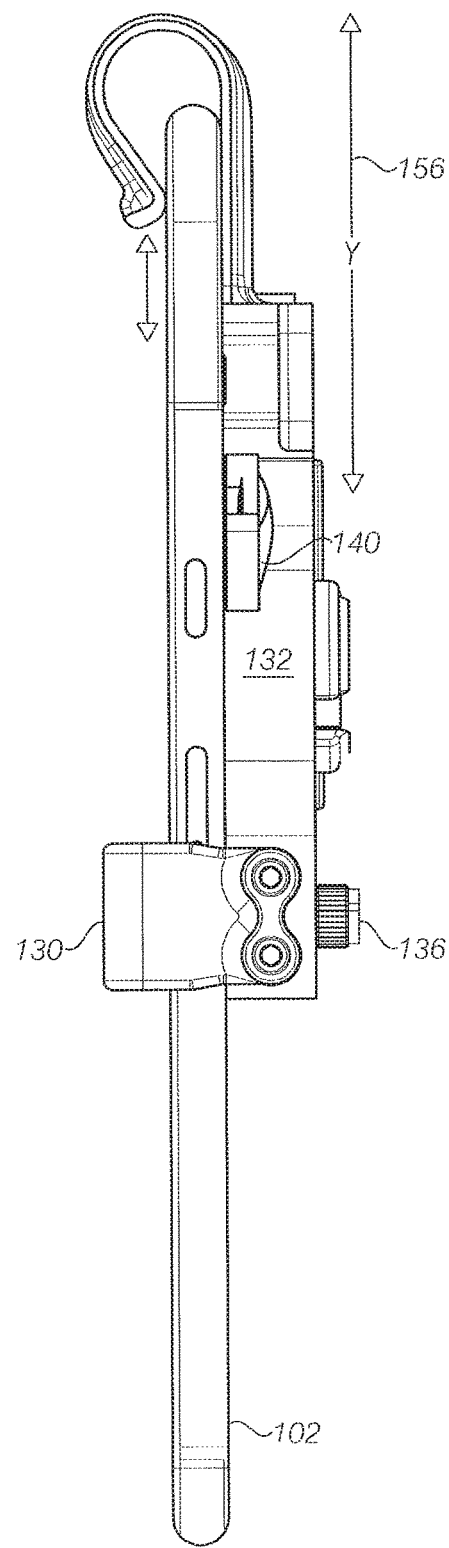
Figure 25C:
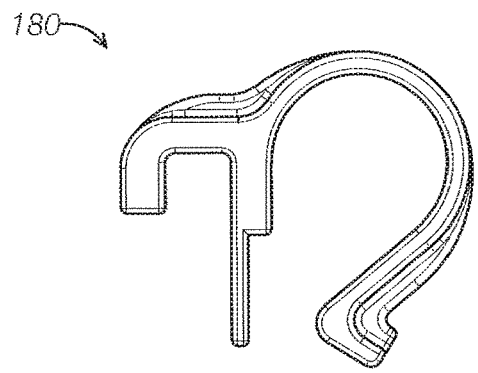
FIGS. 25C-25G illustrate additional features of embodiments of anterior adapters described herein.
Figure 25D:
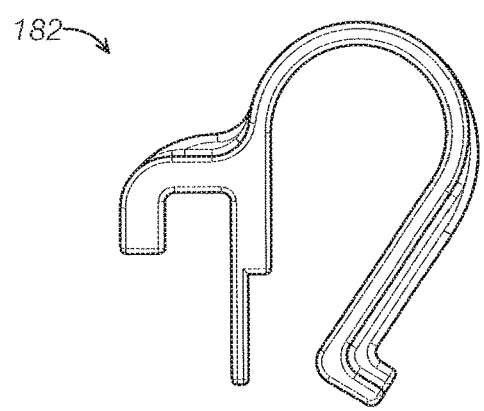
Figure 25E:
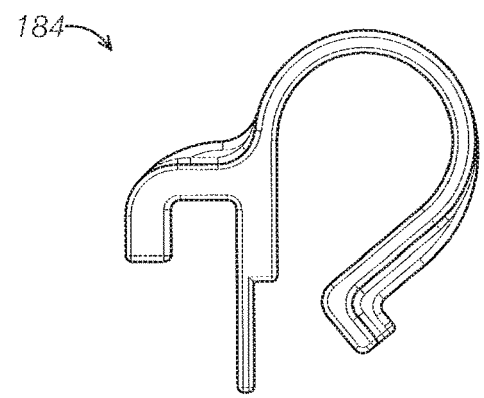

FIGS. 25A and 25B illustrate additional embodiments of an anterior adapter 100 with alternate configuration for the third engagement structure. The illustrate third engagement structures 138' have different lengths to accommodate movement of the adapter relative to hand held computer device along the y-axis 156 to line up the optical axis of the camera with the optical axis of the macro-lens 140 or ophthalmoscopy lens 110. The adapters 100 can be provided with multiple sizes of third engagement structures 138/138' so that the end user can removably engage the third engagement structure 138/138' having the appropriate geometry based on the camera location of the hand held computer device. FIGS. 25C-25E illustrate third engagement structures 180, 182, and 184, respectively, with varying geometry. The adapters described herein can include multiple geometries of third engagement structures that can be removably engaged with the anterior adapter 104 based on the geometry and location of the camera 134 of the hand held computer device 102.

Figure 25F:
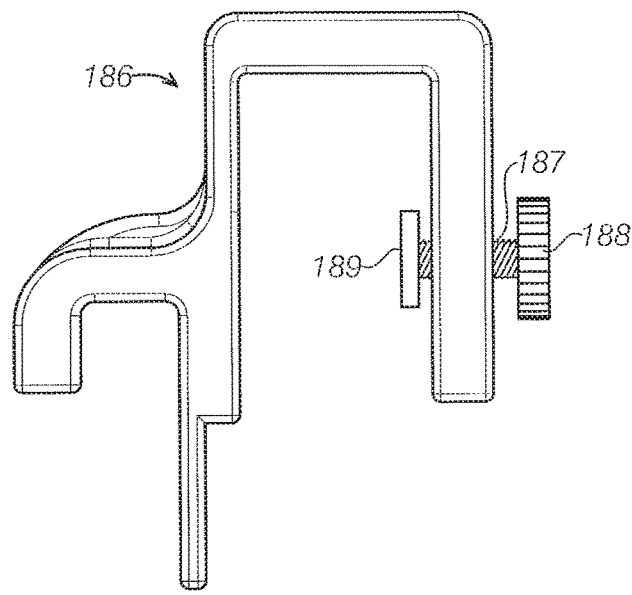
Figure 25G:
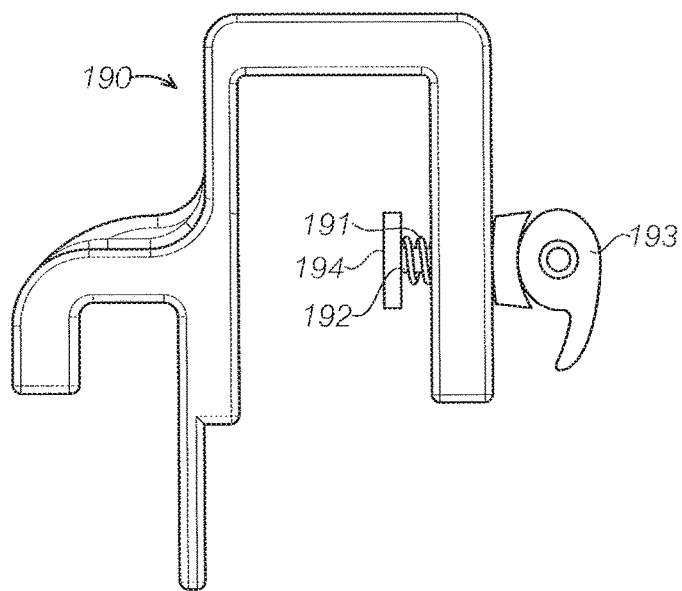

FIG. 25F illustrates a third engagement structure 186 with an adjustable engagement structure including a screw 187, knob 188, and soft padding 189 for engaging the hand held computer device 102. FIG. 25G illustrates a third engagement structure 190 with an adjustable engagement structure including a spring 191, quick release shaft 192, quick release lever 193, and padding 194 for engaging the hand held computer device 102. In some embodiments the adjustable third engagement structures 186, 190 shown in FIGS. 25F-25G can be used instead of the clamp 130 and third engagement structure 138 used in other embodiments. Thus, in this alternate configuration a single contact point can be used to secure the anterior adapter portion 104 to the hand held computer device 102.

Figure 26A:
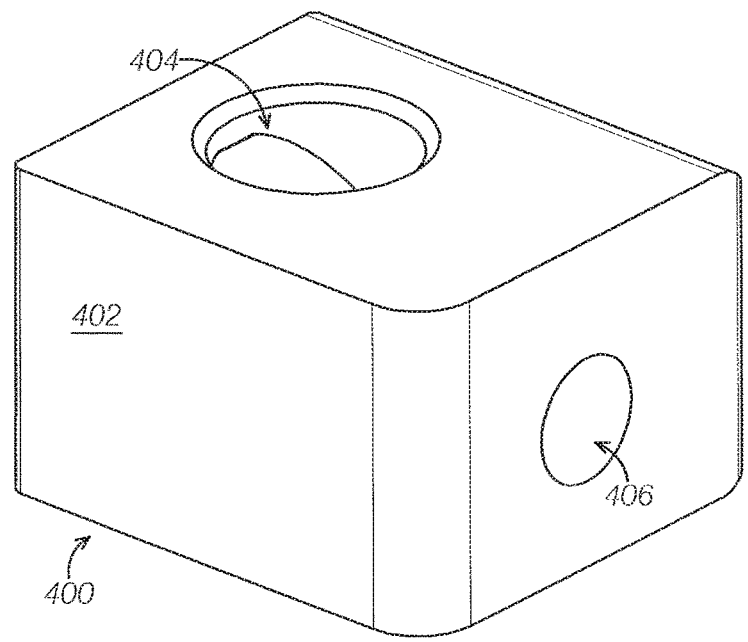
FIGS. 26A and 26B illustrate an exterior view and cross-sectional view, respectively, of a removable beam splitter module in accordance with some embodiments.
Figure 26B:
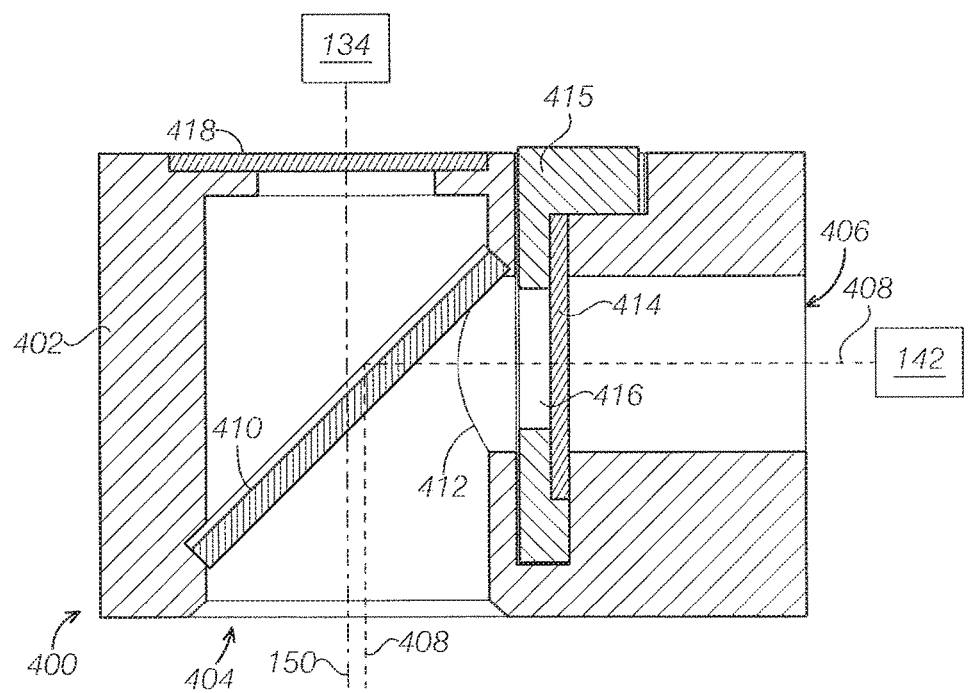

FIGS. 26A and 26B illustrate an exterior view and cross-sectional view, respectively, of a removable beam splitter module 400 in accordance with some embodiments. FIGS. 26C and 26D illustrate the beam splitter module 400 separate from and engaged with an anterior adapter 104, respectively, in accordance with some embodiments. The beam splitter module 400 includes an exterior housing 402, opening 404, and light source opening 406. Light emitted from the adjustable light source 142 enters the beam splitter module 400 along light path 408 through light source opening 406 and is reflected off of mirror 410 to be coaxial with the optical axis 150 of the camera 134. The beam splitter module 400 can also include a polarizing filter 414, polarizing holder 415, and pinhole 416 along the light path 408. The beam splitter can also include an optional lens 412 to further modify the light path 408 of the light emitted from the adjustable light source 142. In one example the optional lens 412 can condense the light into a circular shape. The beam splitter module 400 can also include a polarizing filter 418 adjacent to the camera 134. The anterior adapter 104 illustrated in FIGS. 26C and 26D has a light source 142 that emits light in the direction of the dominant axis of the clamp 130. In this embodiment, the light source within the anterior adapter is oriented such the light is emitted laterally into the side of the beam splitter module 400. The beam splitter module 400 allows the anterior adapter 104 to capture images with the camera 134 through a pupil of the eye that is not dilated thereby enabling direct ophthalmoscopy of the retina of the patient.

Figure 26E:
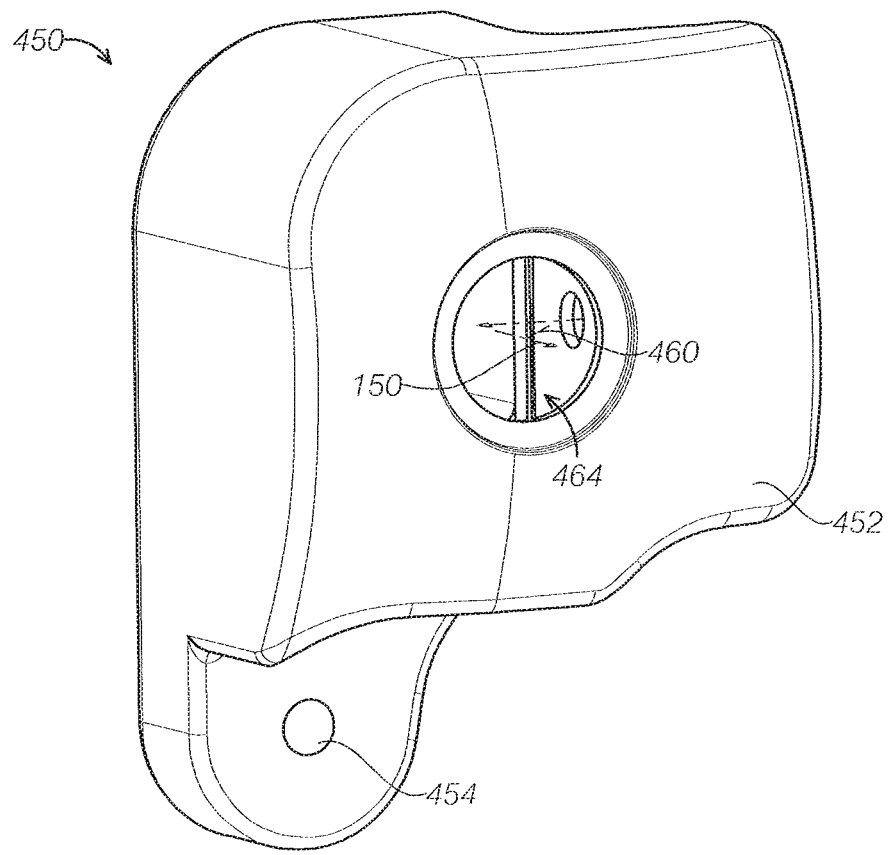
FIGS. 26E and 26F illustrate a front and back view respectively of a beam splitter module in accordance with some embodiments.
Figure 26F:
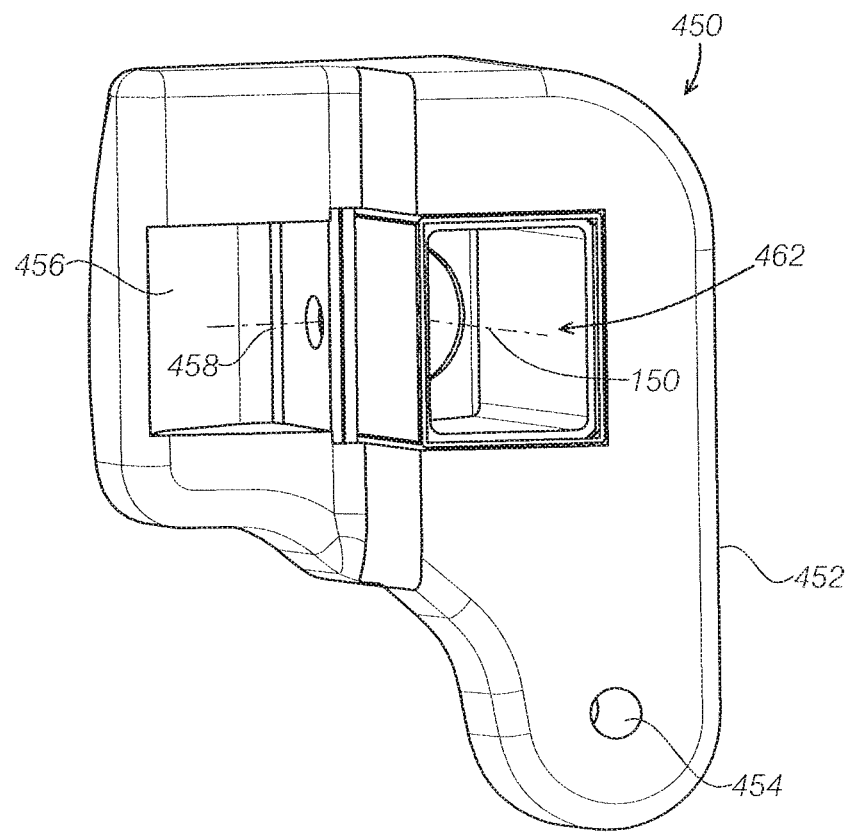

FIGS. 26E and 26F illustrate another embodiment of a beam splitter module 450 that is adapted to receive light from the light source 142 orthogonally to the body 132 of the anterior adapter 104. The removable beam splitter module 450 includes 452 and a hinge or pivot 454 that can in some embodiments removably engage with the hinge 141. The removable beam splitter module 450 can rotate about the hinge or pivot 454 to position the removable beam splitter module 450 adjacent to the adjustable light source 142 or out of the optical path of the light source. The removable beam splitter module 450 includes a first mirror 456 that reflects the light along pathway 458 towards the second mirror 460. After the light reflects off of the second mirror 460 the light path 458 is coaxially with the optical pathway 150 of the camera 134 of the hand held computer device 102. The removable beam splitter includes an opening 460 for the light path 458 to exit the module such that the light path 458 to be coaxial with the optical pathway 150 of the camera 134 of the hand held computer device. The removable beam splitter includes an opening 462 adapted to be positioned adjacent to the camera 134.

Figure 27A:
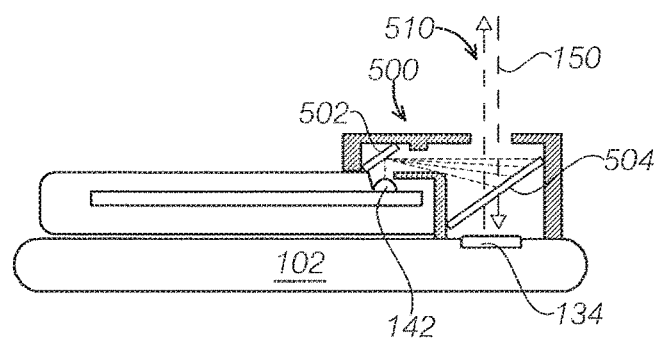
FIG. 27A illustrates an anterior adapter engaged with an embodiment of a beam splitter module in accordance with some embodiments.

FIG. 27A illustrates an anterior adapter engaged with an embodiment of a beam splitter module 500. The beam splitter module 500 includes a first mirror 502 and second mirror 504. The beam splitter module 500 can removably engage with the anterior adapter such that the light source 142 of the anterior adapter portion is directed along pathway 510 in line with the optical axis 150 of the camera 134 of the hand held computer device 102. The beam splitter module 500 can include optional polarizing filters along the optical pathway of the light source 142 and/or optical pathway of the camera 134.

Figure 27B:
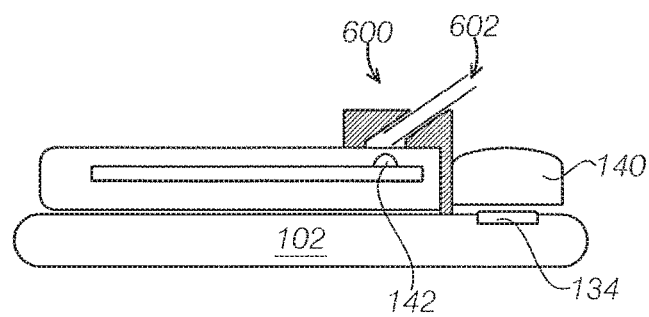
FIG. 27B illustrates an anterior adapter engaged with an embodiment of a slit lamp module in accordance with some embodiments.

FIG. 27B illustrates an anterior adapter engaged with an embodiment of a slit beam module 600 including a slit lamp 602 to direct the light diagonally from the light source 142 of the anterior adapter.

Figure 27C:
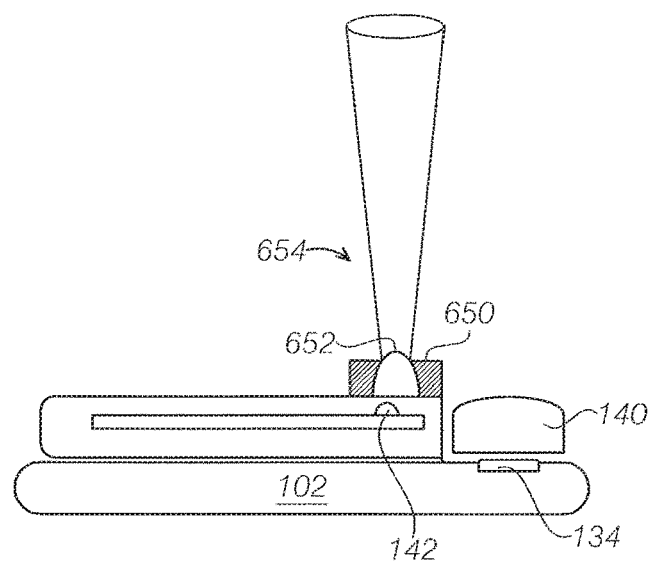
FIG. 27C illustrates an anterior adapter engaged with an embodiment of a collimated beam module in accordance with some embodiments.

FIG. 27C illustrates an anterior adapter engaged with an embodiment of a light beam collimation or condensation module 650. The collimation module 650 can removably engage with the anterior adapter. The collimation module 650 includes a light collimating element 652 that directs the light from the light source 142 to focus the light along light path 654.

Figure 27D:
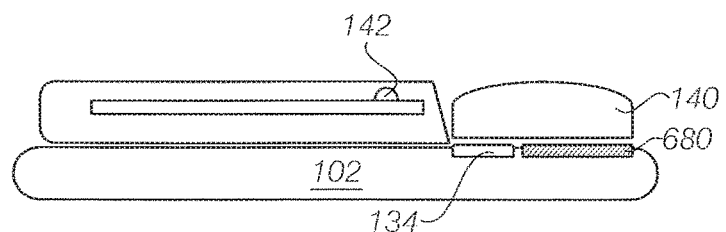
FIG. 27D illustrates an anterior adapter engaged with an embodiment of a mask module in accordance with some embodiments.

FIG. 27D illustrates an anterior adapter engaged with an embodiment of a mask module 680. The mask module 680 can assist users in lining up the camera 134 with the macro lens 140 and optical pathway of the adapter. The mask module 680 is an extension of the anterior adapter portion that includes a small aperture through which the user aligns the camera 134.

Figure 28B:
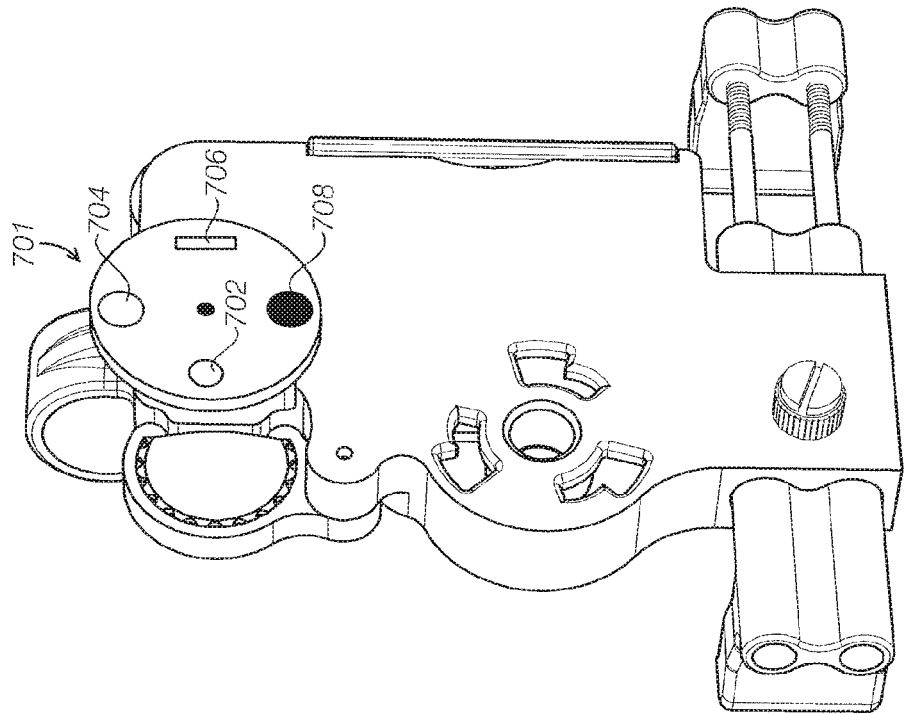
FIGS. 28A-28D illustrate embodiments of modules with multiple lenses that can be used with the adapters described herein.
Figure 28A:
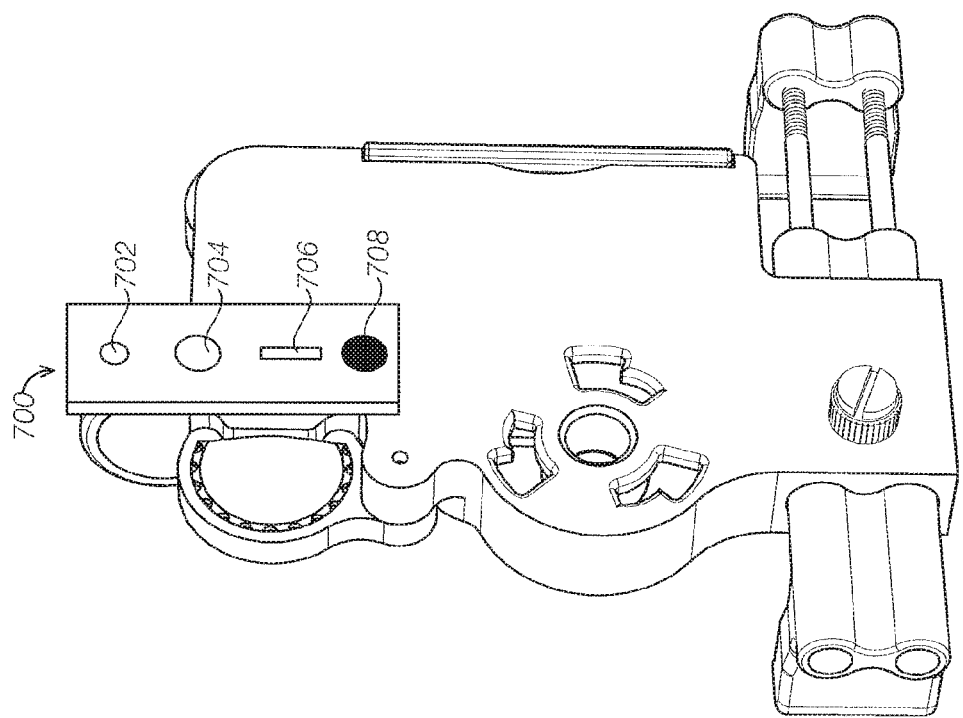
Figure 28C:
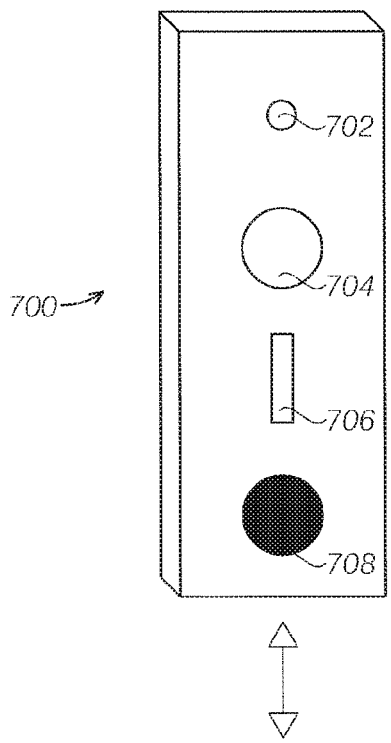
Figure 28D:
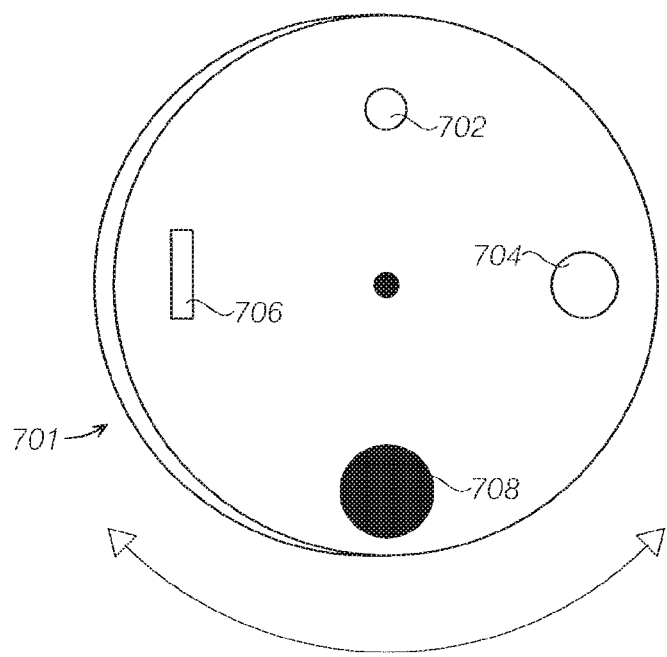

FIGS. 28A-28D illustrate embodiments of modules with multiple lenses that can be used with the adapters described herein. FIGS. 28A and 28C illustrate a module 700 with a small aperture lens 702, large aperture lens 704, slit lamp 706, and blue filter 710. The module 700 can move along the y-axis 156 to position the desired small aperture lens 702, large aperture lens 704, slit lamp 706, or blue filter 710 in front of the light source 142. FIGS. 28B and 28D illustrate a module 701 with a circular shape including a small aperture lens 702, large aperture lens 704, slit lamp 706, and blue filter 710. The module 701 can be rotated to position the desired small aperture lens 702, large aperture lens 704, slit lamp 706, or blue filter 710 in front of the light source 142. The modules 700, 701 can be removable.

FIG. 29A illustrates an adapter 104 with a posterior portion 800 having an integral telescoping optical pathway enclosure. The posterior portion 800 includes a first section 802, second section 804, and optional visor 806 that adds additional protection from overhead or ambient light. The second section can removably receive the ophthalmoscopy lens 110 or come with the ophthalmoscopy lens 110 built into the second section 804. The second section 804 can move relative to the first section 802 to adjust the length between the anterior adapter 104 and the ophthalmoscopy lens 110 (not shown). The illustrated posterior portion 800 includes a connection element 808 configured to removably engage with the anterior adapter 104. The illustrated posterior portion 800 includes a magnet to secure the posterior portion 800 relative to the anterior adapter 104. The magnets can be designed to engage and line up the posterior portion 800 with the anterior adapter 104, with optional grooves one or both the posterior portion 800 and the anterior adapter 104 that facilitate proper optical alignment.

FIG. 29B illustrates an adapter 104 with a posterior portion 900 having an integral telescoping optical pathway enclosure. The posterior portion 900 includes a first section 902, second section 904, and optional enclosure 906. The second section can removably receive the ophthalmoscopy lens 110 or come with the ophthalmoscopy lens 110 (not shown) built into the second section 904. The second section 904 can move relative to the first section 902 to adjust the length between the anterior adapter 104 and the ophthalmoscopy lens 110. The illustrated posterior portion 900 includes a connection element 908 configured to removably engage with the anterior adapter 104. The illustrated connection element 908 includes a base that can be removably received by a complementary structure, such as the complementary mating structure 162.

Figure 31A:
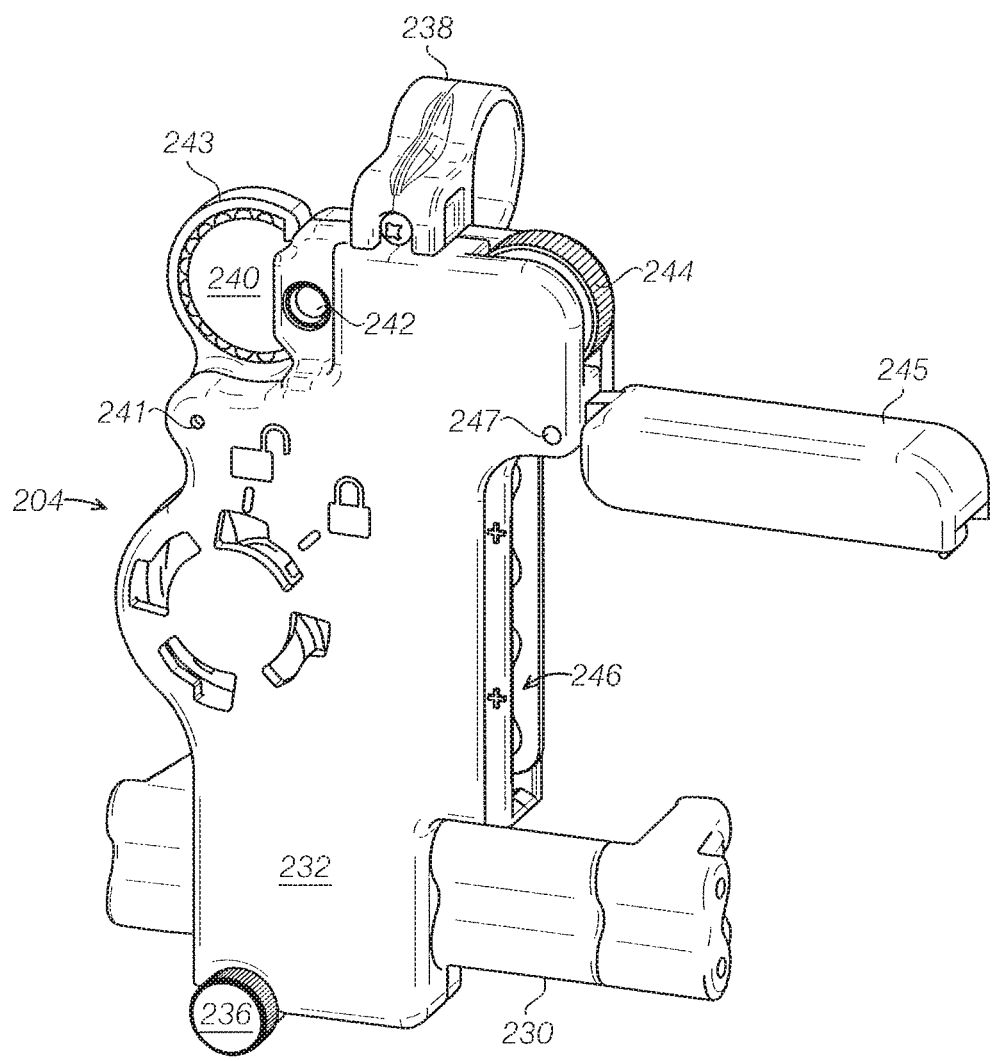
FIGS. 31A and 31B illustrate a front and back view of an anterior adapter portion in accordance with some embodiments.
Figure 31B:
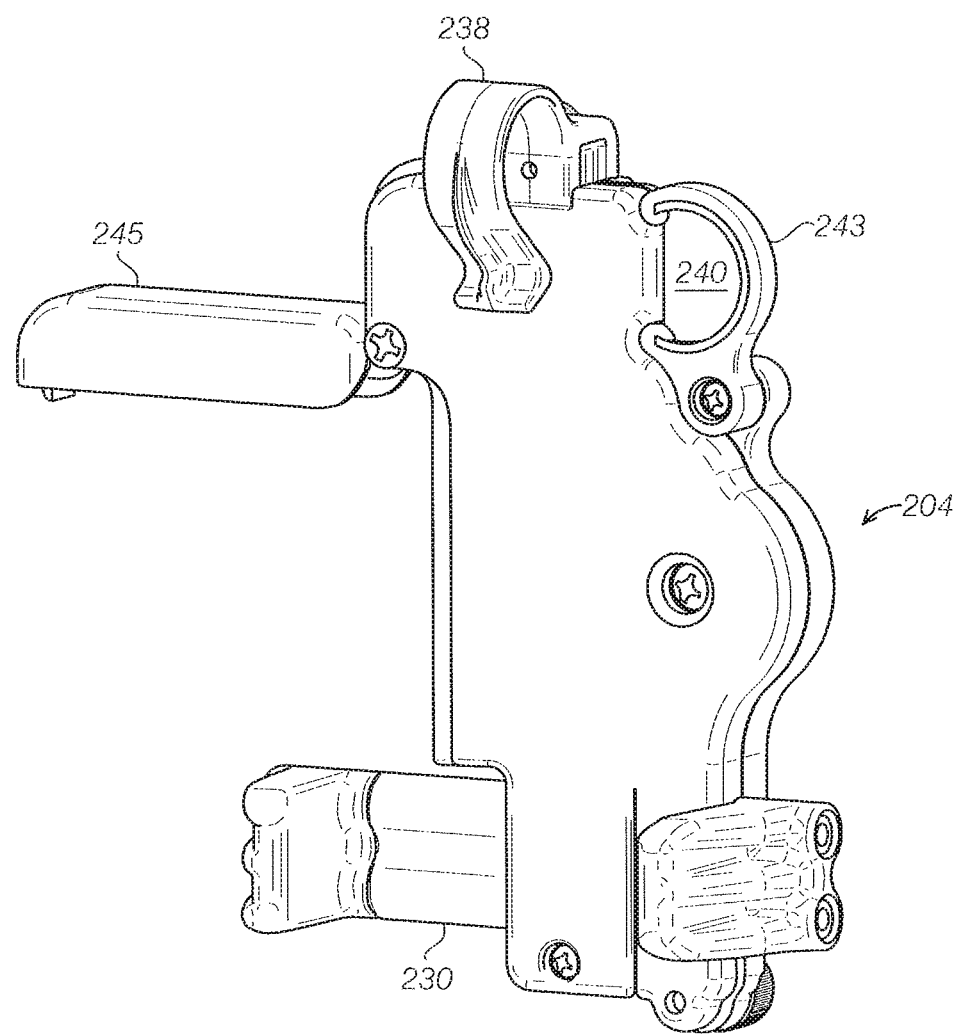
Figure 32A:
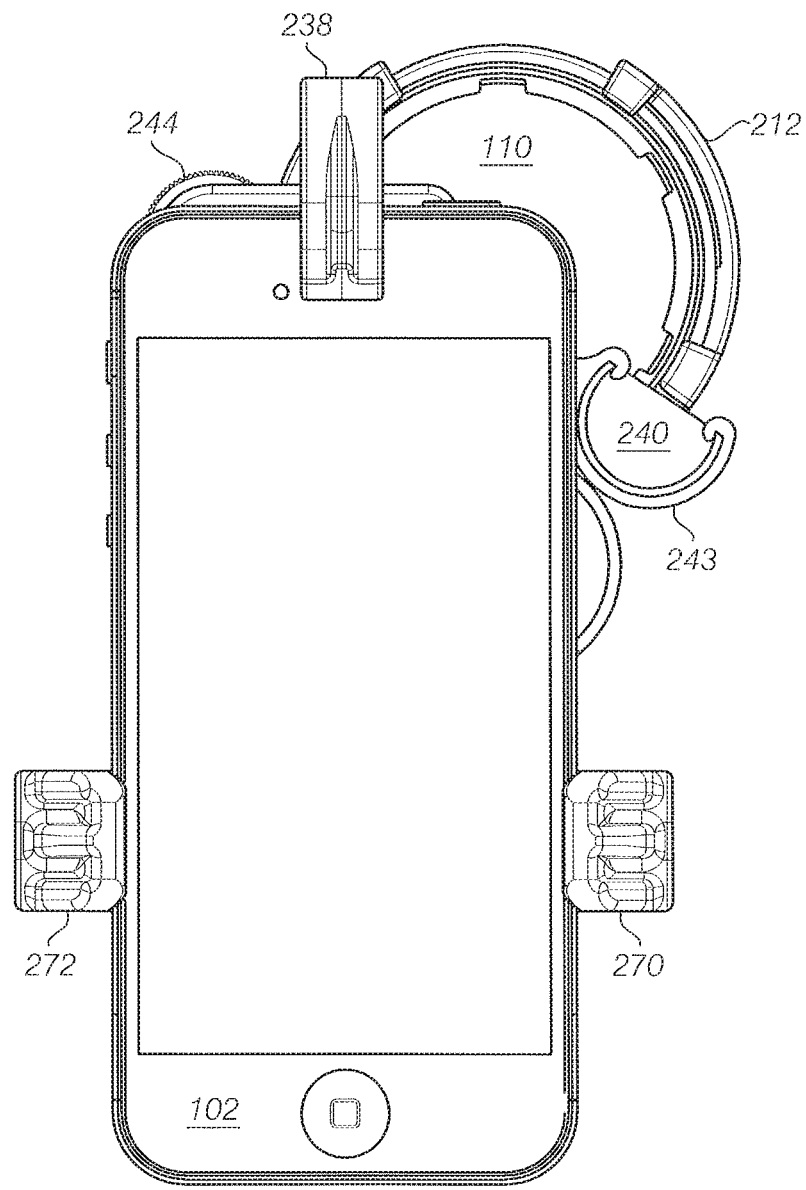
FIGS. 32A and 32B illustrate a front and back view, respectively of an adapter engaged with a hand held computer device in accordance with some embodiments.
Figure 32B:
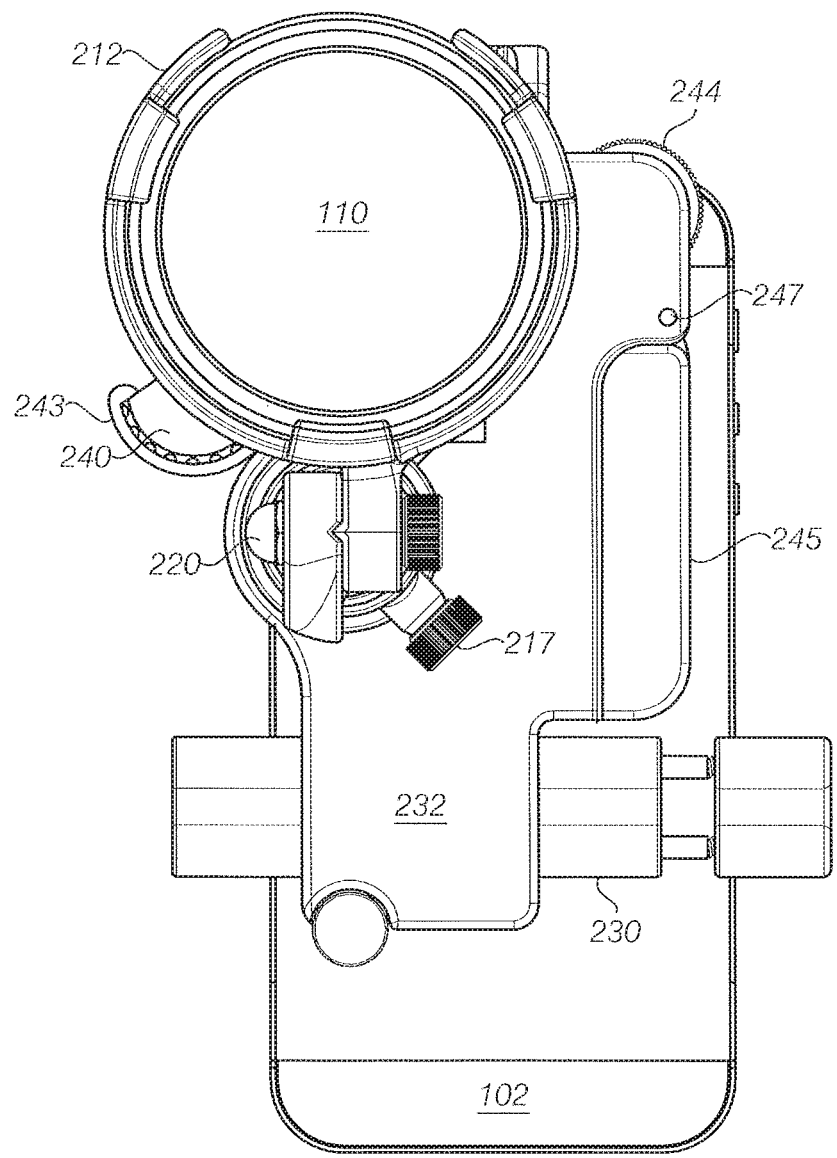
Figure 33A:
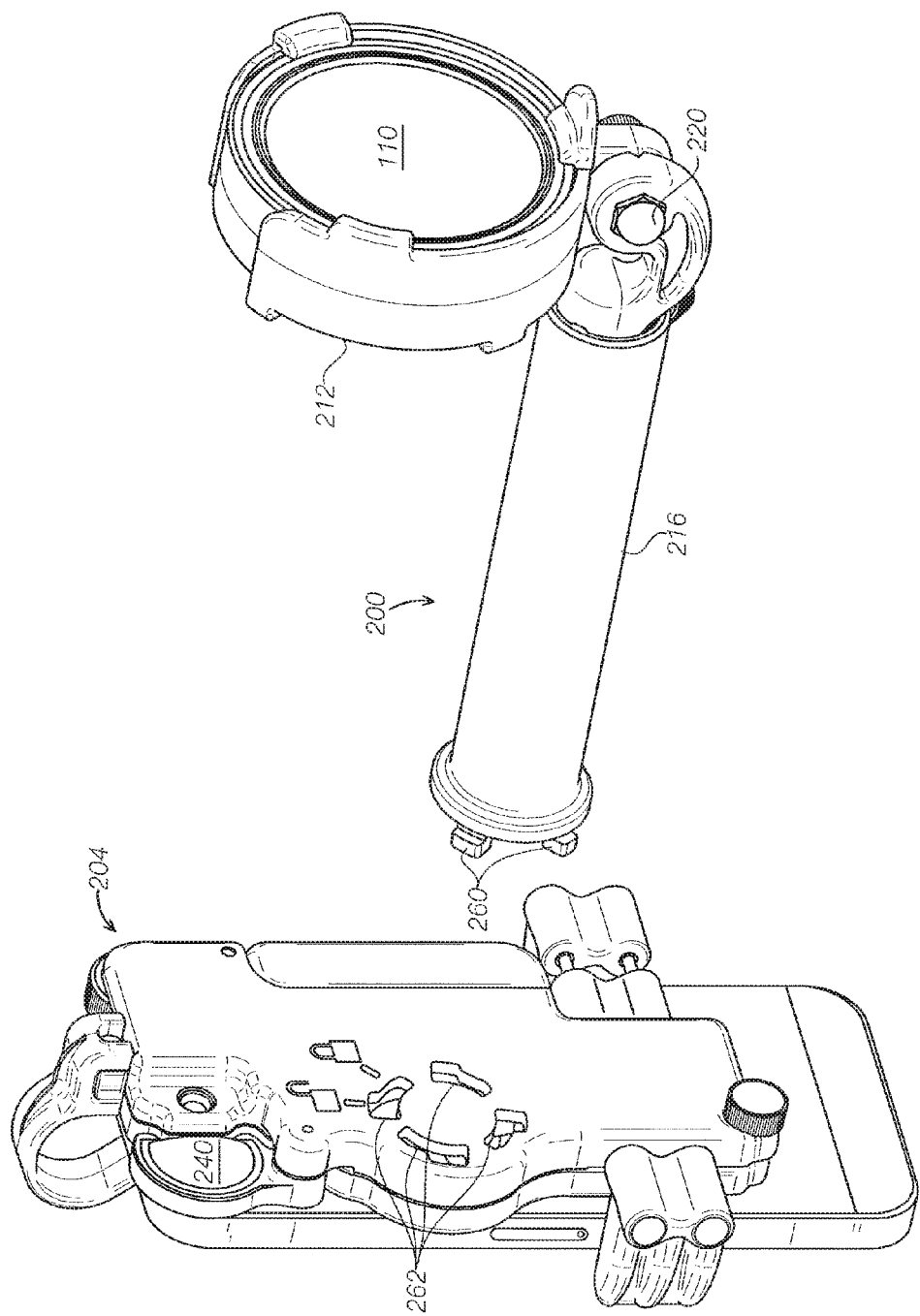
Figure 33B:
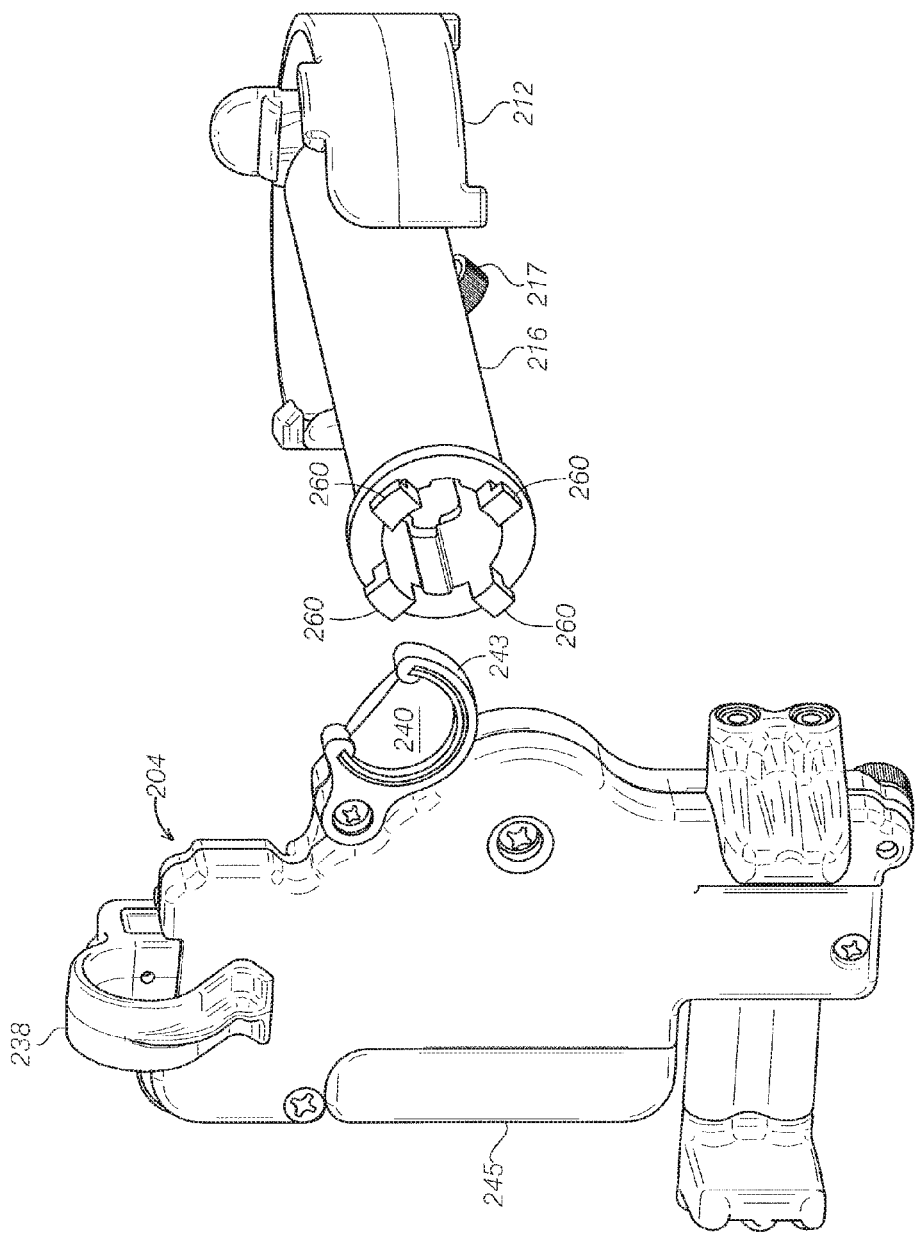

FIGS. 30A-30D, 31A-31B, 32A-32B, and 33A-33C illustrate additional views of embodiments of the adapter 200 described herein. The adapter 200 includes an anterior adapter portion 204 and a removably engageable posterior portion 206. The adapter 200 is generally similar to the adapter 100 but with some modifications to the shape of the base 232 and other features of the adapter 200. The anterior adapter portion body 232 can be secured relative to the horizontal clamp 230 by a locking mechanism 236, such as the illustrated adjustable screw. The horizontal clamp 230 includes a first clamp surface 270 and a second clamp surface 272 adapted to engage with the hand held computer device 102. The illustrated adapter 200 includes a third engagement surface or vertical contact point 238, illustrated with a hook type configuration to hold the hand held computer device 200 flush with the anterior adapter portion 204. The illustrated anterior adapter portion 204 also includes a macro lens 240, macro lens holder 243, lens holder hinge 241, light source 242, and light source dial control 244. The illustrated light source 242 is a LED. The lens holder 243 can be adapted to receive other types of lenses. The anterior adapter portion 204 includes a battery door 245, battery compartment 246, and battery door hinge 247. FIGS. 31A and 31B illustrate the battery door 245 in an open position showing the battery compartment 246.

The posterior portion 206 includes a lens 110 (such as an ophthalmoscopy lens) and lens holder 212. The posterior portion 206 can include a base shaft 216 and telescoping shaft (shown in a retracted position) configured to move relative to one another to modify the length of the posterior portion 206. The adjustable screw 220 can also be configured to lock the movement of the telescoping shaft relative to the base shaft 216 in some embodiments. A telescoping section locking mechanism 217, which is illustrated as a thumb screw can be used to adjust the length of the posterior section 206 and restrict relative movement between the base shaft 216 and telescoping section. The illustrated posterior portion 206 includes a male engagement structure 260 shown with four prongs. The male engagement structures is configured to engage with a complementary female mating structure 262 of the anterior adapter portion 204. The prongs can engage with the complementary structure and be rotated to lock into position.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements, these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical range recited herein is intended to include all sub-ranges subsumed therein.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. An adapter configured to engage with a hand held computer device with a camera having an optical axis comprising:

an anterior adapter portion comprising: a body, a clamp configured to engage with the hand held computer device at a first location and a second location, a lens holder engaged with a macro lens movable between a first position in the optical axis of the camera and a second position outside of the optical axis of the camera, an adjustable light source with a light axis parallel to a macro lens optical axis, a third engagement surface configured to slidably engage with the hand held computer device at a third location, and a complementary surface of the body configured to reversibly engage with a base section of a posterior portion, wherein the clamp defines an axis and the body of the anterior adapter portion is configured to move along the axis of the clamp; and the posterior portion comprising: the base section configured to reversibly engage with the complementary surface of the body of the anterior adapter portion, a telescoping section movable relative to the base section, and a lens holder engaged with a distal end of the telescoping section configured to removably engage with an ophthalmoscopy lens, the base section configured to removably engage with the body of the anterior adapter portion to form an optical axis between the ophthalmoscopy lens and the camera of the hand held computer device.

2. The adapter of claim 1, further comprising: a lens holder hinge engaged with the telescoping section of the posterior portion and the lens holder, the lens holder hinge adapted to move the lens holder between a first position in the optical axis of the camera and a second position outside of the optical axis of the camera.

3. The adapter of claim 2, wherein the second position includes the lens holder folded flush with the telescoping section.

4. The adapter of claim 1, wherein the adapter has an open optical pathway between the lens holder and camera.

5. The adapter of claim 1, wherein the third engagement surface has a semi-circular or hook shape configured to slidably engage with the hand held computer device at the third location.

6. The adapter of claim 5, wherein the third engagement surface is adapted to hold a surface of the body of the anterior adapter against a surface of the hand held computer device.

7. The adapter of claim 1, further comprising: a removable enclosure configured to removably engage with the posterior portion.

8. The adapter of claim 7, wherein the removable enclosure includes a clamping mechanism to engage with the posterior portion.

9. The adapter of claim 7, the removable enclosure further comprising: a telescoping portion configured to adjust a length of the removable cover.

10. The adapter of claim 7, the removable enclosure further comprising a proximal portion with an opening to accommodate the camera of the hand held computer device and the light source of the anterior adapter portion and a distal section to engage with the lens holder.

11. The adapter of claim 7, wherein the removable enclosure is adapted to encase the optical pathway between the camera and the lens holder.

12. The adapter of claim 1, further comprising an ophthalmoscopy lens engaged with the lens holder, the ophthalmoscopy lens configured for indirect ophthalmoscopy.

13. The adapter of claim 12, wherein the ophthalmoscopy lens is a lens in the range of 10 D to 90 D.

14. The adapter of claim 1, wherein the macro lens has a dominant plane orthogonal to the optical axis of the macro lens, the macro lens having a non-circular cross-sectional profile in the dominant plane.

15. The adapter of claim 1, wherein the adjustable light source is integral with the body of the anterior adapter and powered by a power source within the anterior adapter.

16. The adapter of claim 1, wherein the light source comprises a light-emitting diode (LED).

17. The adapter of claim 1, further comprising a light diffuser.

18. The adapter of claim 1, further comprising: a light source control on the anterior adapter portion configured to adjust the properties of the light source.

19. The adapter of claim 17, wherein the light source control comprises a dial.

20. The adapter of claim 1, wherein the clamp includes a first surface configured to engage with the first location of the hand held computer device and a second surface configured to engage with the second location of the hand held computer device.

21. The adapter of claim 20, wherein the first surface and second surface are on opposing sides of the hand held computer device.

22. The adapter of claim 1, further comprising: an anterior locking mechanism on the anterior adapter portion configured to position the anterior body relative to the axis of the clamp.

23. The adapter of claim 22, wherein the anterior locking mechanism is adapted to secure a length of the axis of the clamp.

24. The adapter of claim 23, wherein the anterior locking mechanism is configured to secure the first surface of the clamp relative to the second surface of the clamp.

25. The adapter of claim 1, further comprising: a posterior locking mechanism configured to secure the telescoping section relative to the base section.

26. The adapter of claim 1, further comprising: a lens holder locking mechanism configured to secure the lens holder relative to an axis of the telescoping section.

27. The adapter of claim 22, wherein the locking mechanism comprises a thumb screw.

28. The adapter of claim 1, further comprising: a battery compartment within the body of the anterior adapter portion.

29. The adapter of claim 1, wherein the clamp is spring loaded.

30. The adapter of claim 1, wherein the clamp is configured to apply a compressive force to the first and second location.

31. The adapter of claim 1, further comprising a beam splitter module configured to removably engage with the anterior adapter, the beam splitter module when engaged with the anterior adapter configured to direct light from the adjustable light source to be coaxial with the optical axis of the camera.

32. The adapter of claim 31, wherein the beam splitter includes a mirror to reflect light from the adjustable light source to be coaxial with the optical axis of the camera.

33. The adapter of claim 31, the beam splitter module further comprising: a polarizing light filter in the optical pathway of the adjustable light source when the beam splitter module is engaged with the anterior adapter portion and a polarizing light filter in the optical pathway of the camera when the beam splitter module is engaged with the anterior adapter portion.

34. The adapter of claim 1, further comprising a slit beam module configured to removably engage with the anterior adapter that refracts and filters the light emitted by the light source into a rectangular slit shape.

35. The adapter of claim 1, further comprising a cobalt blue filter adapted to be positioned over the LED and/or the camera lens when the anterior adapter portion is engaged with the hand held computer device.

36. The adapter of claim 1, wherein the hand held computer device is a smartphone, tablet computer, or mobile imaging device.

37. The adapter of claim 1, wherein the third engagement structure is configured to removably engage with the anterior adapter portion.

38. The adapter of claim 37, the third engagement structure further comprising: an adjustable engagement mechanism configured to engage with the hand held computer device.

39. The adapter of claim 38, the adjustable engagement mechanism further comprising: a thumb screw and a hand held computer engagement surface.

40. The adapter of claim 38, the adjustable engagement mechanism further comprising: a spring, a hand held computer engagement surface, and a release lever.

41. The adapter of claim 1, further comprising: a light shaping module configured to be removably engaged with the anterior adapter portion to modify the adjustable light source.

42. The adapter of claim 41, wherein the light shaping module includes a plurality of light shaping structures.

43. The adapter of claim 42, wherein the light shaping module comprises: a first aperture, a second aperture that is larger than the first aperture, a slit lamp, and a blue filter.

44. The adapter of claim 1, wherein the telescoping section has a closed optical pathway.

45. The adapter of claim 1, wherein the base section includes a magnet to engage with the anterior adapter portion.

46. A method of obtaining images of an eye of a patient, the method comprising:
attaching an anterior adapter portion to a hand held computer device having a camera, the anterior adapter comprising: a body, a clamp configured to engage with the hand held computer device at a first location and a second location, a lens holder engaged with a macro lens movable between a first position in the optical axis of the camera and a second position outside of the optical axis of the camera, an adjustable light source with a light axis parallel to a macro lens optical axis, a third engagement surface configured to slidably engage with the hand held computer device at a third location, and a complementary surface of the body configured to reversibly engage with a base section of a posterior portion, wherein the clamp defines an axis and the body of the anterior adapter portion is configured to move along the axis of the clamp;
adjusting a position of the body of the anterior adapter relative to the axis of the clamp to line up the macro lens optical axis with the optical axis of the camera of the hand held computer device;
obtaining an image of the eye of the patient with the camera of the hand held computer device using the macro lens and the adjustable light source;
engaging a posterior portion to the anterior adapter portion by engaging the base section of the posterior portion with the complementary surface of the body of the anterior adapter portion, the posterior portion comprising: a telescoping section movable relative to the base section, and a lens holder engaged with a distal end of the telescoping section configured to removably engage with an ophthalmoscopy lens, the base section configured to removably engage with the body of the anterior adapter portion to form an optical axis between the ophthalmoscopy lens and the camera of the hand held computer device; and
obtaining an image of the eye of the patient with the camera of the hand held computer device and the ophthalmoscopy lens.

47. The method of claim 46, further comprising: locking the position of the body of the anterior adapter after adjusting the position of the body of the anterior adapter relative to the axis of the clamp to line up the macro lens optical axis with the optical axis of the camera of the hand held computer device.

48. The method of claim 46, further comprising: engaging an ophthalmoscopy lens with the lens holder prior to obtaining the image of the eye of the patient with the camera of the hand held computer device and the ophthalmoscopy lens.

49. The method of claim 48, further comprising: engaging a removable cover with the posterior portion to encase an optical pathway between the ophthalmoscopy lens and the camera of the hand held computer device.

50. The method of claim 46, further comprising adjusting the adjustable light source of the anterior adapter portion to illuminate the eye of the patient with a desired amount of light.

51. The method of claim 46, further comprising: engaging a beam splitter module with the anterior adapter, the beam splitter module configured to removably engage with the anterior adapter, the beam splitter module when engaged with the anterior adapter configured to direct light from the adjustable light source to be coaxial with the optical axis of the camera.

52. The method of claim 51, further comprising: obtaining a direct ophthalmoscopy image of the eye of the patient with the camera of the hand held computer device and the beam splitter module.

53. The method of claim 46, further comprising: engaging a slit beam module with the anterior adapter, the slit beam module configured to removably engage with the anterior adapter portion.

54. The method of claim 53, further comprising: obtaining an image of the eye of the patient with the slit beam module.

55. The method of claim 46, wherein the hand held computer device is a smartphone, tablet computer, or mobile imaging device.

* * * * *